(12) United States Patent
Travers et al.

(10) Patent No.: US 9,833,617 B2
(45) Date of Patent: Dec. 5, 2017

(54) APPARATUS AND METHOD FOR TREATING MULTIPLE TUMORS IN PATIENTS WITH METASTATIC DISEASE BY ELECTRIC FIELDS

(71) Applicant: Loyalty Based Innovations, LLC, Longwood, FL (US)

(72) Inventors: Peter F. Travers, Longwood, FL (US); Ken Watkins, Lake Mary, FL (US); Timothy VanderMey, Altamonte Springs, FL (US)

(73) Assignee: Loyalty Based Innovations, LLC, Longwood, FL (US)

( * ) Notice: Subject to any disclaimer, the term of this patent is extended or adjusted under 35 U.S.C. 154(b) by 0 days.

(21) Appl. No.: 14/795,597

(22) Filed: Jul. 9, 2015

(65) Prior Publication Data

US 2016/0022986 A1     Jan. 28, 2016

Related U.S. Application Data

(60) Provisional application No. 62/028,996, filed on Jul. 25, 2014.

(51) Int. Cl.
| | | |
|---|---|---|
| *A61N 1/32* | (2006.01) | |
| *A61N 1/04* | (2006.01) | |
| *A61N 1/372* | (2006.01) | |
| *A61N 1/40* | (2006.01) | |

(52) U.S. Cl.
CPC ............. *A61N 1/32* (2013.01); *A61N 1/0476* (2013.01); *A61N 1/37217* (2013.01); *A61N 1/40* (2013.01)

(58) Field of Classification Search
CPC ............ A61N 1/32; A61N 1/0476; A61N 1/40
See application file for complete search history.

(56) References Cited

U.S. PATENT DOCUMENTS

| | | |
|---|---|---|
| 6,443,978 B1 | 9/2002 | Zharov |
| 6,868,289 B2 | 3/2005 | Palti |
| 7,089,054 B2 | 8/2006 | Palti |
| 7,146,210 B2 | 12/2006 | Palti |
| 8,019,414 B2 | 9/2011 | Palti |
| RE43,618 E | 8/2012 | Palti |
| 8,406,870 B2 | 3/2013 | Palti |
| 8,465,533 B2 | 6/2013 | Palti |
| 8,706,261 B2 | 4/2014 | Palti |
| 2003/0097152 A1 | 5/2003 | Palti |
| 2005/0209640 A1* | 9/2005 | Palti ........................ A61N 1/40 607/2 |

(Continued)

OTHER PUBLICATIONS

Notification of Transmittal of the International Search Report and the Written Opinion of the International Searching Authority, or the Declaration dated Oct. 16, 2015 for International Application No. PCT/US20151040009 (11 pages).

*Primary Examiner* — Eric D. Bertram
(74) *Attorney, Agent, or Firm* — Taylor IP, P.C.

(57) ABSTRACT

An insulated electrode system for delivering a plurality of tumor treating electromagnetic fields including an array of electrode elements for proximate location on a body of a patient. Each electrode element of the array having an insulation layer. Each electrode element being independently electrically accessible and configured to be dynamically assigned to emanate an electromagnetic field relative to at least one other of said electrode elements.

19 Claims, 29 Drawing Sheets

(56) References Cited

U.S. PATENT DOCUMENTS

| | | |
|---|---|---|
| 2008/0097530 A1 | 4/2008 | Muccio et al. |
| 2008/0188846 A1* | 8/2008 | Palanker ............... A61B 18/14 606/32 |
| 2012/0184800 A1 | 7/2012 | Brighton |
| 2013/0184637 A1 | 7/2013 | Palti |
| 2013/0184674 A1 | 7/2013 | Palti |
| 2013/0296995 A1 | 11/2013 | Mahmood et al. |

* cited by examiner

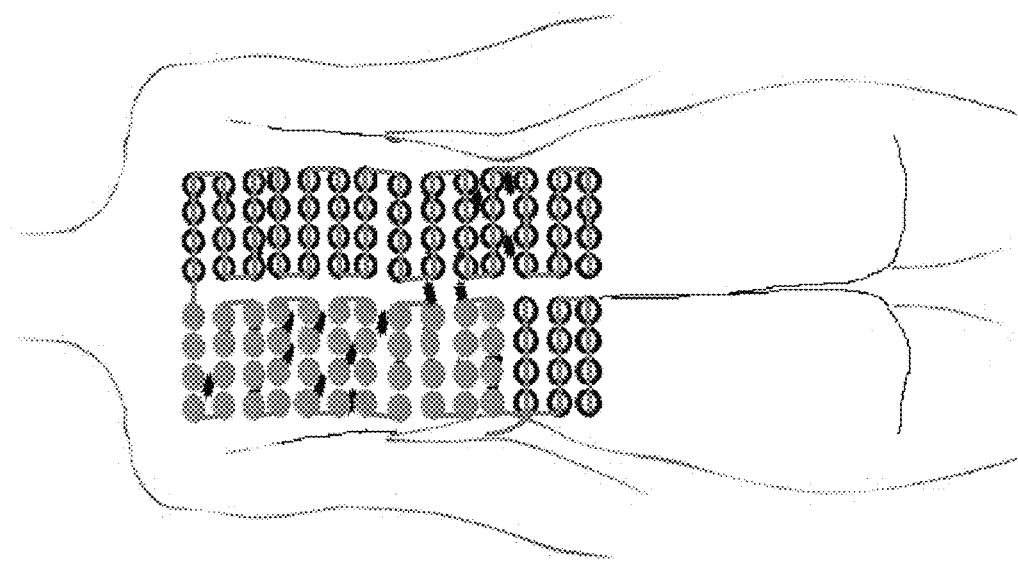
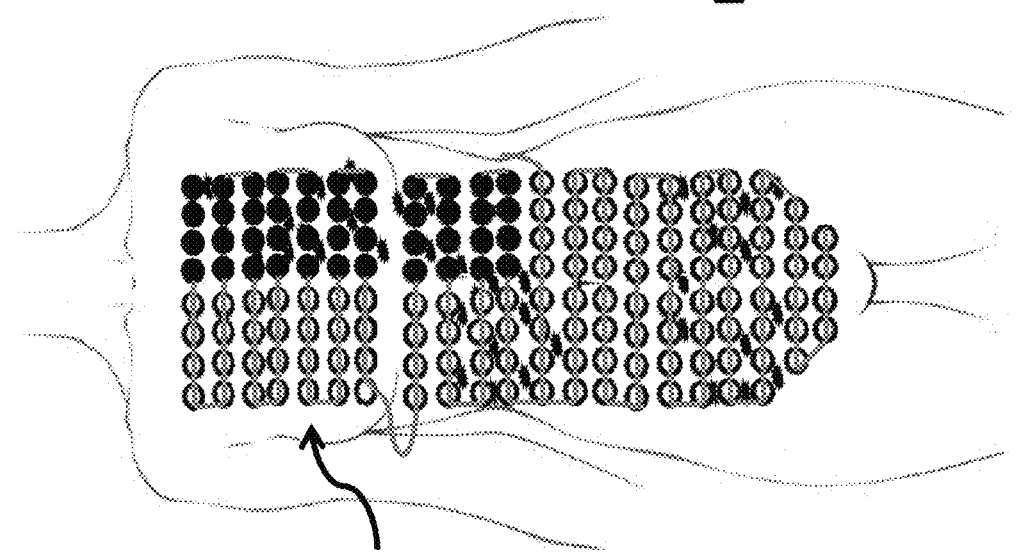
Fig 19

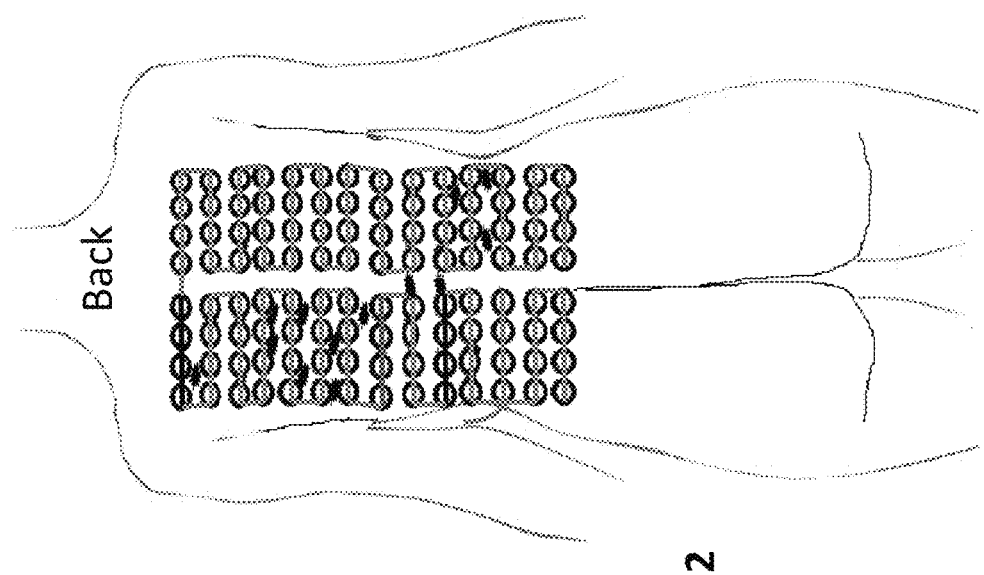
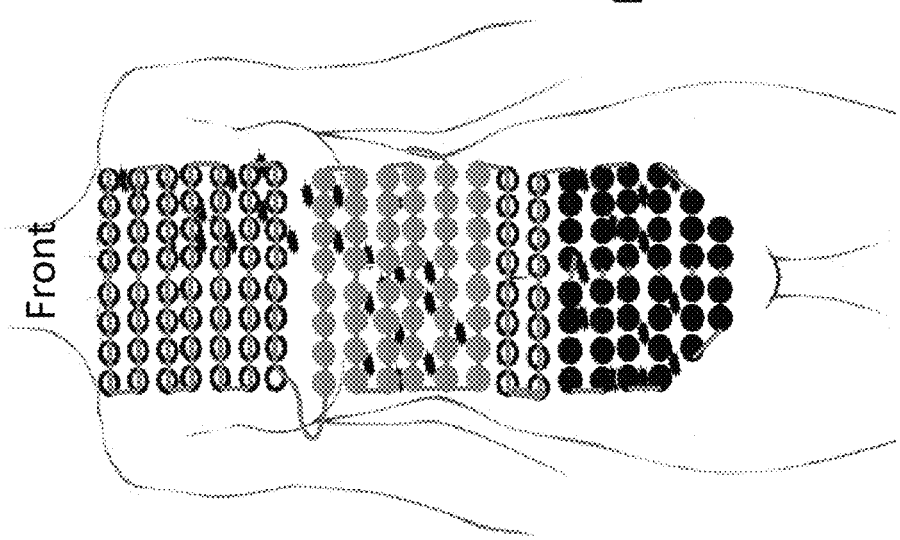
Fig 22

APPARATUS AND METHOD FOR TREATING MULTIPLE TUMORS IN PATIENTS WITH METASTATIC DISEASE BY ELECTRIC FIELDS

CROSS REFERENCE TO RELATED APPLICATIONS

This is a non-provisional application based upon U.S. provisional patent application Ser. No. 62/028,996, entitled "APPARATUS AND METHOD FOR TREATING MULTIPLE TUMORS IN PATIENTS WITH ADVANCED METASTATIC DISEASE BY ELECTRIC FIELDS", filed Jul. 25, 2014, which is incorporated herein by reference.

BACKGROUND OF THE INVENTION

1. Field of the Invention

The present invention relates to tumor and cancer cell treatment and more specifically to treatments involving the application of electromagnetic fields.

2. Description of the Related Art

Alternating Electric Fields, also referred to as Tumor Treating Fields (TTF's), can be employed as a type of cancer treatment therapy by using low-intensity electromagnetic fields. These low-intensity fields rapidly change direction, thousands of times per second. Since the TTF's are electric fields, they do not cause muscle twitching or severe adverse side effects on other electrically activated tissues. The growth rate of metastatic diseases is typically greater than the growth rate of normal, healthy cells. Alternating Electric Fields therapy takes advantage of this high growth-rate characteristic. TTF's act to disrupt a cancer cell's mitotic process and cytokinesis by manipulating the cell's polarizable intracellular constituents, namely tublins that form mitotic spindles that pull the genetic material in the nucleus into tow sister cells. TTF's interrupt mitotic spindle microtubule assembly thereby preventing cell division. The metastatic disease cells treated using TTF's will go into programmed cell death usually within 4 to 5 hours. The result is a significant reduction in tumor size and potential for full elimination of solid tumors. TTF's are tuned to treat specific cancer cells and thereby do not damage normal cells. TTF therapy can be used as a sole treatment method, or it can be combined with conventional drug delivery mechanisms.

TTF's are applied to patients using insulated electrodes adhered to the skin by a variety of methods including the use of medical adhesives, articles of clothing, etc. There are multiple configurations of insulated electrodes, but all have an insulated material with a high dielectric constant on one side and a thin metal coating on the other, usually silver. Insulated electrodes used to generate TTF's always come in pairs with both sides being similar, but not necessarily the same.

Referring now to FIG. 1, there is shown a typical insulated electrode array 10 used in the administration of TTF's. The insulated electrode array 10 includes a pair of arrays, 10A and 10B, which are made from smaller insulated electrode sub-elements 12. Because the insulated electrode 10 archetypically works in pairs, there is generally a Sub-array A and Sub-array B, respectively 10A and 10B. Each smaller insulated electrode 12 has an insulating material 14, typically a ceramic that is adhered to the patient. The leads 16 interconnect the smaller insulated electrodes 12 to a main lead line 18, which links to a generator (not shown).

Confusion arises in the prior art when the term insulated electrode is interchanged with the term "Isolect" or just "Electrode". These terms are sometimes used to describe "elements of an array" or entire sets of arrays. It is often not disclosed in the prior art exactly what is meant by any of the above terms. It should be appreciated by persons skilled in the art that insulated electrodes or terms used in exchange for insulated electrodes are generally references to either fixed arrays of smaller dedicated insulated electrode sub-elements 12 as shown in FIG. 1 or to large solid insulated electrodes 20 as shown in FIG. 2.

There are many reasons small insulated electrodes 12 used individually will not work when producing TTF's, a non-exhaustive list includes:

1. Small elements used individually do not draw enough energy to form an electric field that will go through the human torso. For example, 4 amps over an area of approximately 1 square foot may be required to create an effective TT field strong enough to treat cancer tumors in the lungs. Small elements used individually cannot draw the required energy. In other words there is a minimum current density (amps/area) and a minimum area required to be effective. Single small insulated electrodes cannot meet these requirements. Placing small electrodes into an array close together and energizing them at the same time so that they act as one insulated electrode solves this problem.
2. If a small element was designed to carry enough energy to go through the lungs (e.g., 4 amps/sq. ft.), the resulting concentration of that much energy in a small area generally causes tingling on the patient's skin making treatment regimen unbearable.
3. If small elements were used individually to produce TTF's, their physical size and shape would create inefficiencies when treating massive areas like cancer spread throughout the pleura membranes. The pleurae, inside the thoracic cavity, generally extend from just below the clavicle area to the lower ribs. Using small individual insulated electrodes would increase the likelihood of gaps in field coverage, which in turn could allow cancer cells to persist.

While large insolated electrodes 20, shown in FIG. 2, produce adequate fields, they have many disadvantages such as the inability to expand when a patient's skin stretches during bending or sitting. Large insulated electrodes 20 also tend to draw more energy at their center, causing tingling similar to that of over-powered smaller insulated electrodes. In contrast, insulated electrodes comprising arrays of smaller insulated electrode sub-elements can deliver energy in a more diffused manner and can adapt to the human body more easily.

Generally, in prior art references processes to choose insulated electrodes in groups, is referring to choosing a smaller group of elements from a larger group. What is typically shown in drawings and is done in practice, is that choosing a smaller number of electrodes from a larger group is for the purpose of wiring the smaller group together in a fixed, dedicated array. In the prior art processes of targeting TTF's from multiple sites to vector a treatment area, it is referring to targeting multiple fixed dedicated arrays or multiple large electrodes. When the prior art references mention sweeping through electrodes to target tumors from different angles, it is referring to energizing different fixed dedicated arrays in a sequential manner. It is generally understood that the prior art refers to fixed dedicated arrays or large electrodes when it discusses manipulating TTF's. Further, the prior art references disclose that insulated electrode sub-elements are dedicated for use in a single array and single power sub-array A or B. This is due to how array elements are wired (see FIG. 1). This creates serious drawbacks when treating patients with metastatic disease.

Referring collectively now to FIGS. 3 and 4, there is shown a typical prior art TTF treatment configuration on a patient with metastatic breast cancer. The metastatic cancer, illustrated as black spots 30, is shown to have spread throughout the pleura around the left lung (FIG. 3). These cancer cells are literally free floating in fluid within the pleura cavity, and are forming many new small tumors. Additionally, there are also small tumors located on the liver.

FIG. 4 shows an insulated electrode array 40 for the left lung and an insulated electrode array 42 for the liver, each including a respective pair, sub-array A and B. The left lung insulated electrode array 40 will fire its sub-array A array 40A with its sub-array B array 40B, and the liver insulated electrode 42 will fire its respective sub-array A array 42A with 42B. Typically, a cross firing of arrays will be programmed to target the cancer from different angles. In the case of cross firing, the front side A array 42A of the liver insulated electrode array 42 will fire with the back sub-array B array 40B of the left lung insulated electrode array 40A, and the front sub-array A array 40A of the lung insulated electrode array 40 will fire with the liver back sub-array B array 42B. However, in the above scenario cross firing may not be possible because of the significant difference in size between the lung and liver insulated electrodes, 40A and 40B. Of course, many other cross-firing combinations can be programmed. The significant limitation of the prior art is that each sub-element 12 of either array 40 or 42 is solely dedicated to its respective home insulated electrode array and to its home sub-array A or B array. In other words, a particular sub-element 12 is solely linked and devoted to its particular insulated electrode array and side and cannot be used except in the function of its home array.

FIG. 5 portrays how cancer cells 30 in the pleura and the liver are actually beginning to shrink, but new cancer cells 30 have appeared in the upper peritoneal cavity above the navel in between the left lung 40 and liver 42 insulated electrode arrays. Likewise, new cancer cells 30 have appeared near the lower peritoneal cavity.

As shown in FIG. 6, to combat the new cancerous growth in between the insulated electrodes, 40 and 42, there needs to be a new insulated electrode array 44 centering the tumors in the upper peritoneal cavity, region 45. This is not possible because it would require placing elements 12 on top of elements 12, as array 44 would overlap with the arrays 40 and 42, which would deny skin contact needed for proper field formation. This limitation in the prior art leads to treatment compromises, putting the patient at risk by failing to treat new tumors as the primary disease. Coplanar fields between the liver and lung are not desirable here because of the significant size difference between the two insulated electrodes, 40 and 42.

Referring now to FIG. 7, there is shown an illustration of a TT field where region 46A is the effective TTF area and region 46B is the ineffective TTF area. This portrays the importance of being able to target each area of tumor growth as a primary concern. TTF's vary in intensity throughout their shape, which can cause significant areas of a field to be below the effective strength. As shown by region 46B, it is possible for tumors to be covered by a field without actually having any beneficial effect because the intensity is not sufficient enough to prevent cell division. In addition, the extreme variance of tissue types and even air pockets within the body can create pockets where field formation is not possible if treatment is attempted from limited directions.

As shown in FIG. 8, continuing with the metastatic breast cancer example shown in FIGS. 4-6, a new insulated electrode array 48 is added to address the new tumor growth in the lower peritoneal cavity. The insulated electrode array 48 is designed to develop a co-planner field (half Moon), horizontally from left to right. In order to form a co-planner field, the array 48 pairs 48A, representing sub-array A, and 48B, representing sub-array B, together in the same front plane of the patient. In TTF best practices it is known that targeting a tumor from different angles increases the effectiveness of tumor reduction. However, prior art treatment with dedicated array elements is compromising the treatment of the patient in this example.

Prior art treatment with dedicated array elements does not have enough versatility to adequately address multiple disease locations. Creating a second co-planner field using the liver insulated electrode array 42 and the lower peritoneal cavity insulated electrode array 48 to create a vertical field cannot be done on the right side because both arrays are dedicated to the A sub-array. Further, multidirectional pairing is not possible because three of the four sub-arrays (40A, 42A and 48A) located on the front side of the patient are solely dedicated to sub-array A. A and B sides are required to establish coupling and field formation. In addition the differing sizes of the liver insulated electrode array 42 and the lower peritoneal cavity insulated electrode array 48 are too dissimilar to form the desired field. Undesired field concentration would occur (twenty-four elements 12 in array 42 to fifteen elements 12 in array 48). Also, the distance to the back liver and lung arrays are too far from the front peritoneal cavity to create an effective field.

In this example the prior art leaves the cancer in the upper peritoneal cavity untreated and the cancer in the lower peritoneal cavity under treated. Such short comings in the prior art can lead to a lack of tumor resolution, unnecessary pain and suffering in the patient, or even death. The prior art is inefficient in that new custom dedicated arrays need to be constantly designed and physically built to address changes in patients with metastatic disease. TTF treatment in the prior art fails the patient, as shown in FIGS. 4-6 and 8, and the patient will likely return to heavy chemotherapy, which can lead to days if not weeks of hospitalization and eventual death. At the time of this writing there does not exist a chemotherapy that does not eventually fail stage 4 patients who become reoccurring and non-responsive. As of 2014 the five year survival rate for stage 4 breast cancer, for example, is only 22% according to the American Cancer Society. A new TTF system needs to be applied in order to treat metastatic disease.

In general TTF treatment using prior art array shapes are determined before they are built. Then, for efficiency reasons, these minimalized array sizes are physically constructed. This however is inefficient when treating metastatic disease because the treatment areas continually change as the cancer spreads. Requiring frequent reconfiguring of arrays. What is needed in the art is the ability to quickly change the configurations of arrays.

When a patient is wearing TTF arrays it is important to ensure adequate warning if any overheating of the elements occurs. The prior art approach generally addresses this concern with temperature sensors that shut off the TTF device if overheating occurs. What is of equal concern is current leakage to the skin. Some patients, desiring the resolution of their disease, may have a tendency to endure warm spots that are actually current leaks. These leaks can cause blistering if not addressed quickly. The electric current levels per element are so low on TTF devices that current leakage can feel much like a warm heating pad. Of course adequately constructing elements to prevent leakage is the first line of defense for this issue. However, TTF arrays are expensive and in some cases can be worn for months at a time to save money. The electrode elements may experience various unknown types of stress during daily activity. It is conceivable that an insulated electrode array may be dropped, etc. The prior art systems lack a current monitoring system.

Array migration and overall warmth of the insulated electrodes can be an issue during TTF treatment. When working with patients with metastatic disease it is more likely that full body arrays will be worn to administer TTFs. When full body TTF arrays are worn during sleep and during other long periods of time it is a challenge to keep them from migrating to less optimal positions. For example, tossing and turning during sleep can exasperate this problem. In addition, warmth from the elements can cause sweating in some cases, which further enables slipping of the arrays as body movement occurs. The prior art has many methods of securing array elements to the skin including various shirts, medical adhesives, etc. These methods are not as successful when used on full-body arrays.

Metastatic disease can literally have dozens of tumor groupings throughout a patient's body. For example, metastatic breast cancer can spread to the lungs, liver, peritoneal cavity, and pancreas all at the same time. Large organs such as the liver can have tumor groupings very far apart. Metastatic disease in the pleura around the lungs and in the peritoneal cavity can pepper large areas of the abdomen with growing cancer cells. Using electric fields on metastatic disease has brought about the need for significant improvements in the application and generation of effective tumor treating fields (TTFs).

What is needed in the art, is a TTF system that enables the dynamic reassignment of array elements to thereby define any array needed and to apply the field from either sub-array A or B.

What is needed in the art is a modular system for adding and removing array elements.

What is needed in the art is a current monitoring sensor that sends a shut off signal to the control device if fluctuations in current, which may be caused by current leakage to the skin or the detachment of the electrode, is detected.

What is needed in the art is a method of adhering array elements to a material while also reducing the temperature of the array elements.

SUMMARY OF THE INVENTION

The present invention provides an improved cancer and tumor treatment regime.

The invention in one form is directed to an insulated electrode system for delivering a plurality of tumor treating electromagnetic fields including an array of electrode elements for proximate location on a body of a patient. Each electrode element having an insulation layer. Each electrode element being independently electrically accessible and configured to be dynamically assigned to emanate an electromagnetic field relative to at least one other of said electrode elements.

The invention in another form is directed to an insulated electrode array for delivering a plurality of tumor treating electromagnetic fields including an array of a plurality of electrode elements each having an insulation layer. Each electrode element being independently programmable and dynamically assignable to a first sub-array then to a second sub-array. A modular system has a plurality of end-to-end element modules incorporating the electrode elements. A control device is configured to dynamically program a frequency range, a firing configuration and a firing sequence for each of the electrode elements. A field generator is configured to generate an electrical signal in the frequency range. There is a flex circuit in electrical communication with both the field generator and the modular system.

The invention in yet another form is directed to a method of delivering tumor treating electric fields to a patient. The method includes the steps of: arranging an insulated electrode element array on the patient; programming a frequency range, a firing configuration and a firing sequence for each electrode element; assigning at least some of the electrode elements to a first sub-array and at least one of the electrode elements to a second sub-array; and dynamically assigning at least one of the electrode elements of the first sub-array to the second sub-array, and at least one of the electrode elements of the second sub-array to the first sub-array.

An advantage of the present invention is that each array element in the inventive device can be redirected to either power sub-array A or B and to any array combination desired and to any frequency desired.

Another advantage of the present invention is that it allows for a universal system that can adapt to body composition and the spread of metastatic disease.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 19 illustrates the second step in the TTF 6-step treatment sequence using dynamic reassignment of array elements;

FIG. 22 illustrates the fifth step in the TTF 6-step treatment sequence using dynamic reassignment of array elements;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
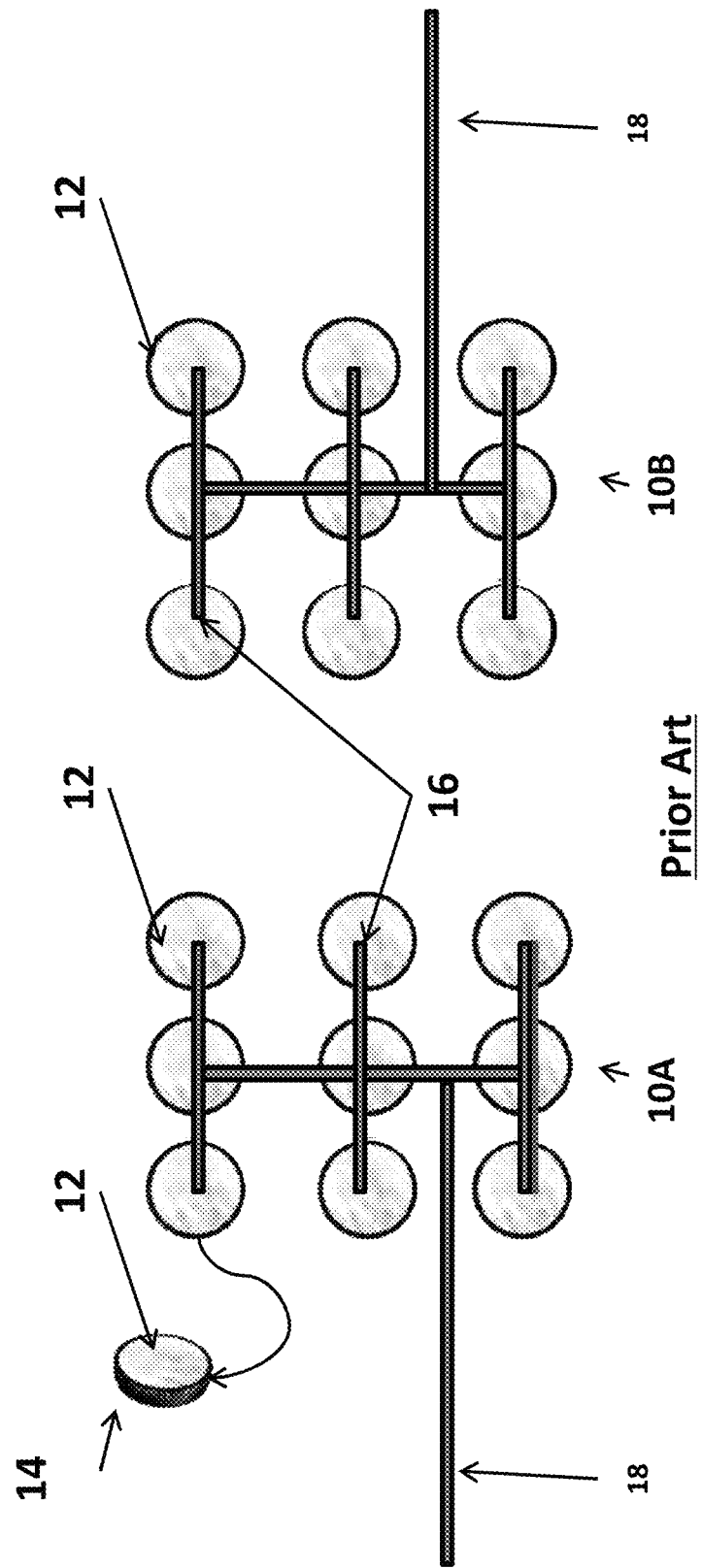
FIG. 1 is an illustration of a prior art insulated electrode array.
Figure 2:
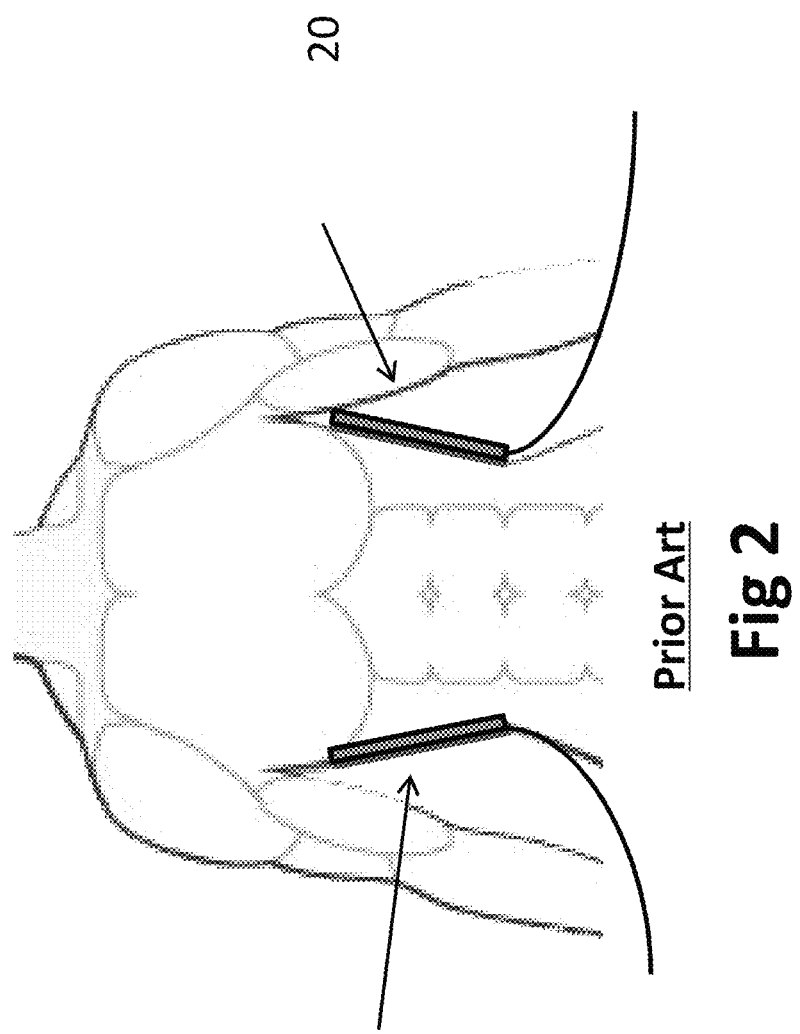
FIG. 2 illustrates large solid insulated electrodes used in the prior art.
Figure 3:
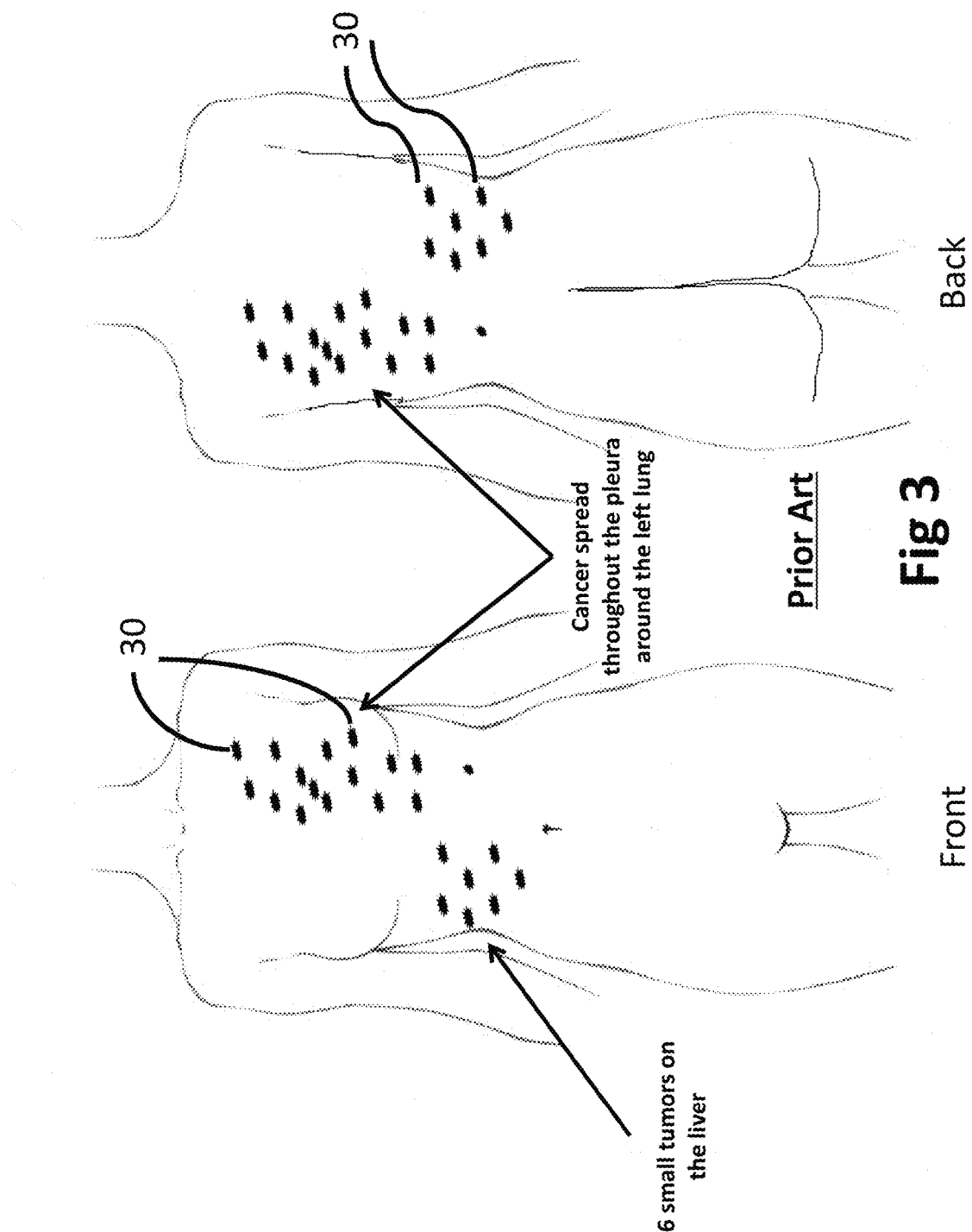
FIG. 3 illustrates tumor locations in a patient.
Figure 4:
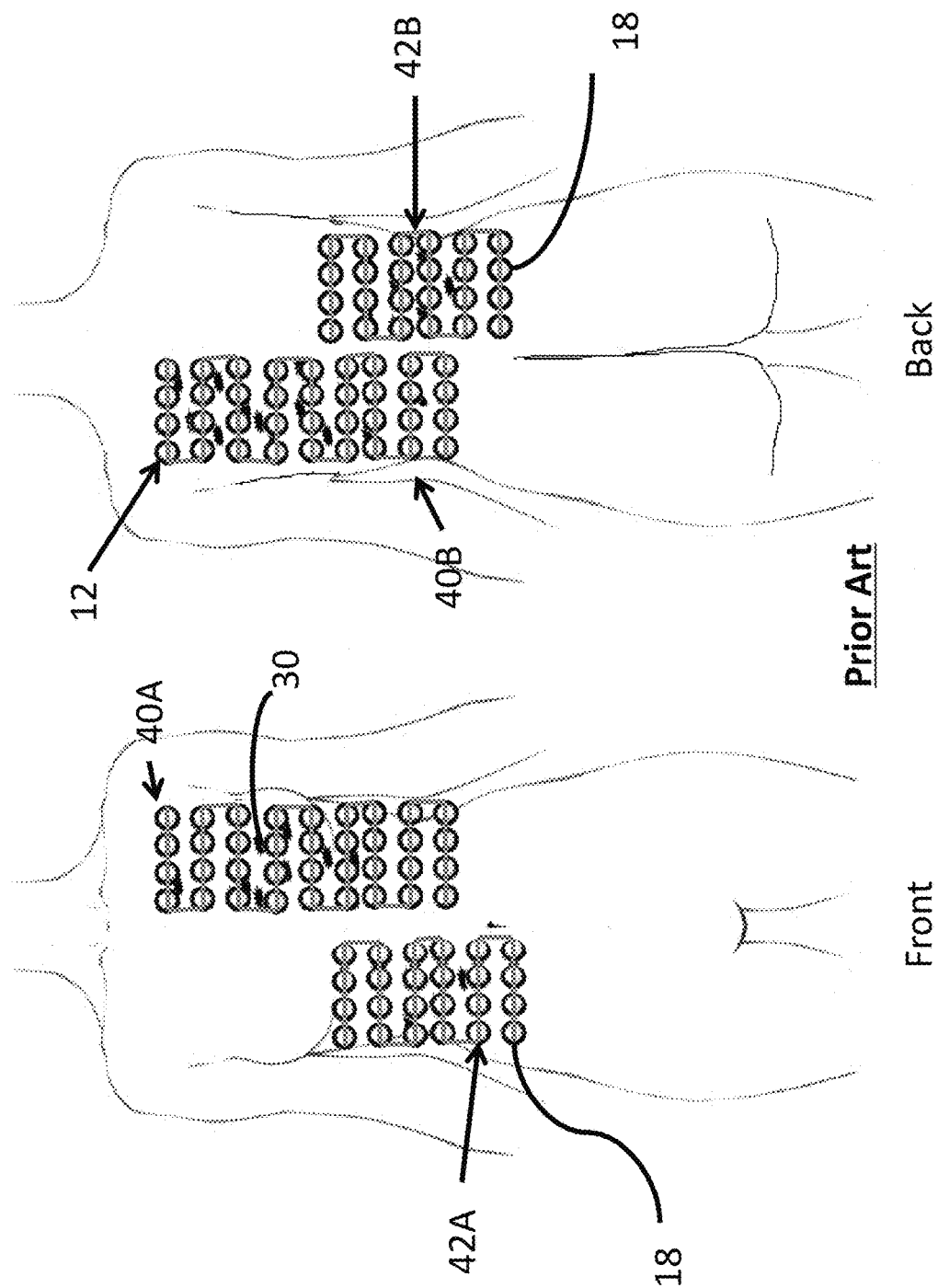
FIG. 4 illustrates the placement of prior art electrode arrays on a patient.
Figure 5:
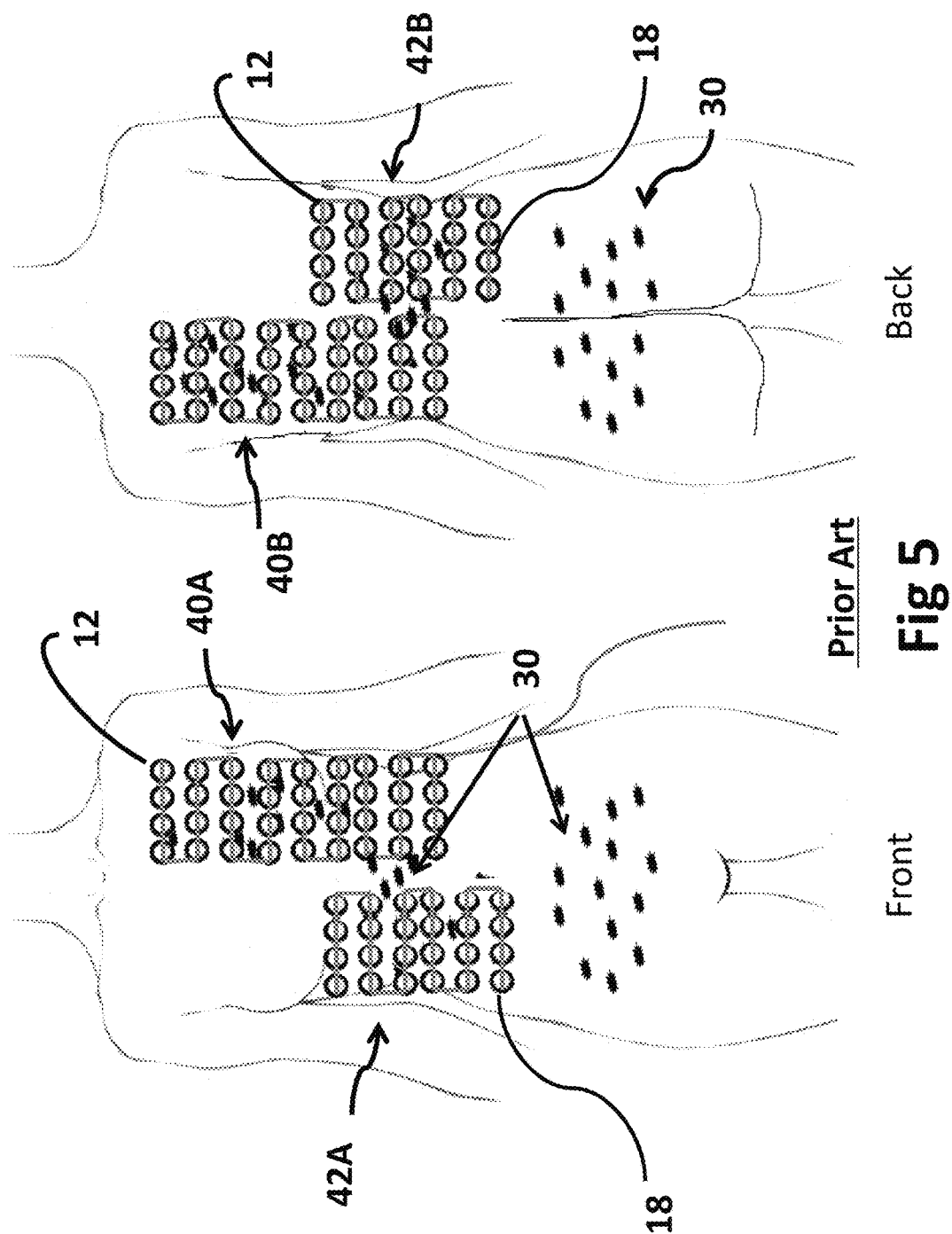
FIG. 5 portrays how cancer cells in the pleura and the liver are beginning to shrink, but new cancer cells having appeared in the upper peritoneal cavity above the navel, in between the left lung and liver, and in the lower peritoneal cavity.
Figure 6:
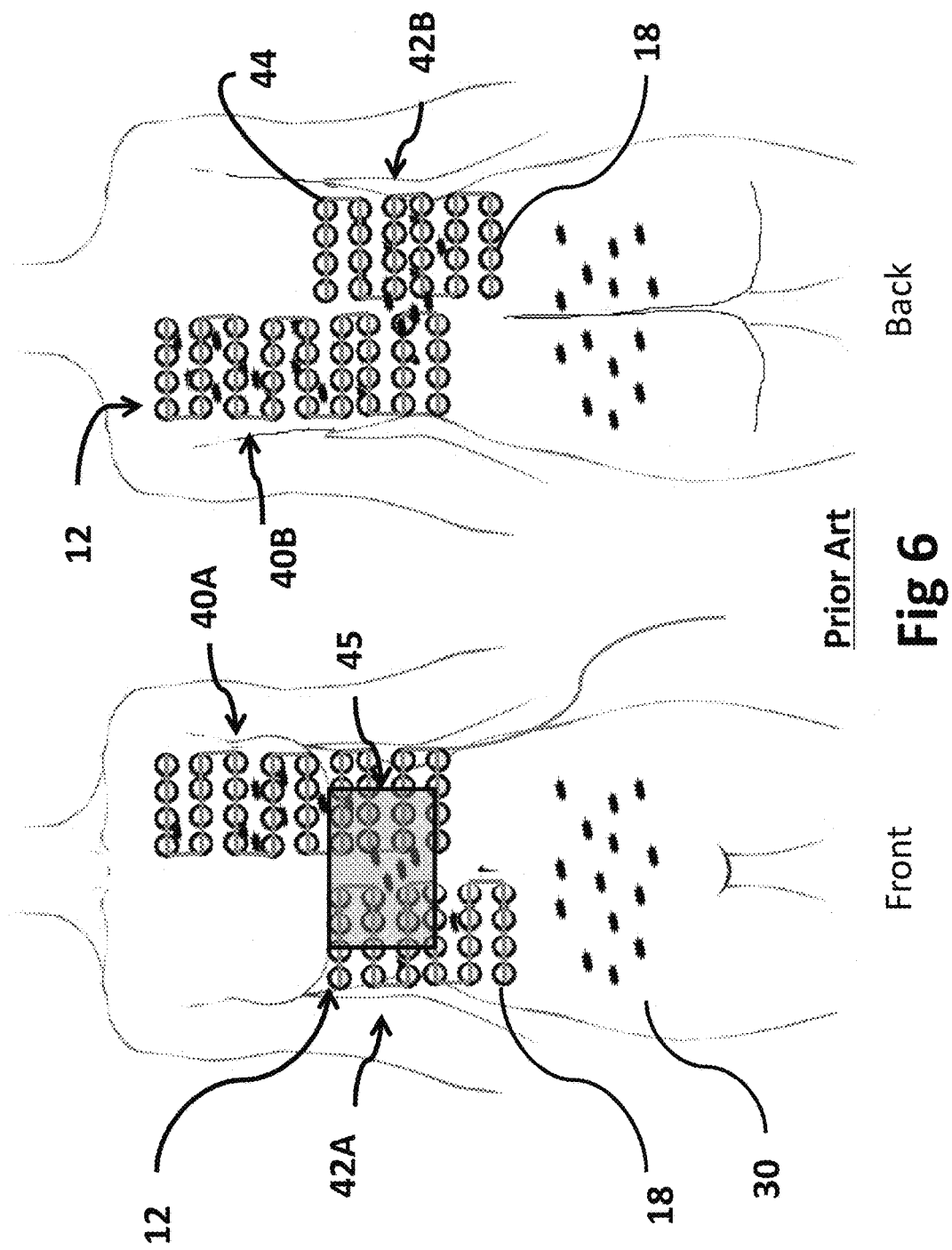
FIG. 6 illustrates the need for a new insulated electrode array centered on the tumors in the upper peritoneal cavity, and the difficulty in adapting the prior art.
Figure 7:
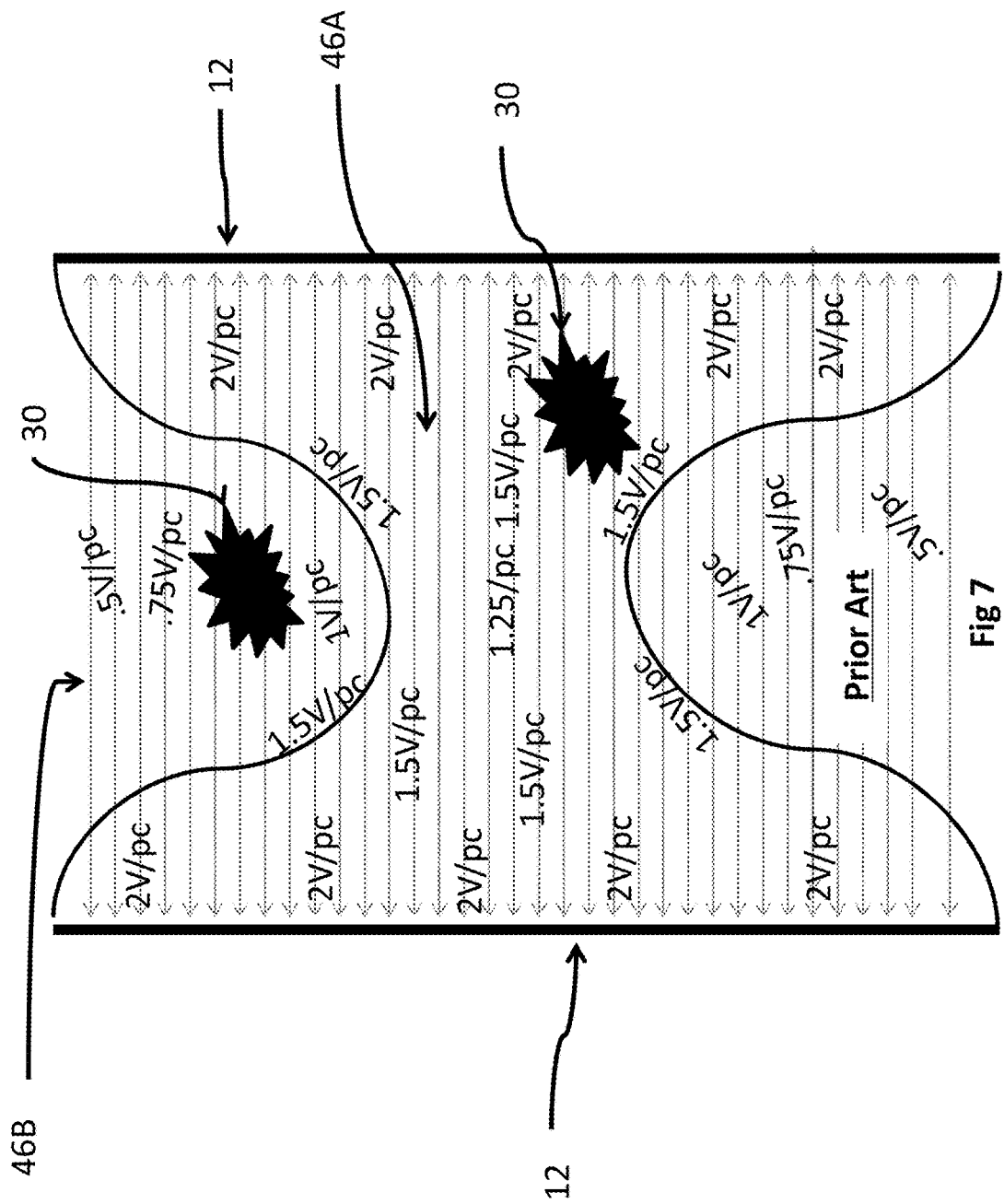
FIG. 7 illustrates a TT field where there is an effective region and an ineffective region of treatment in the prior art systems.
Figure 8:
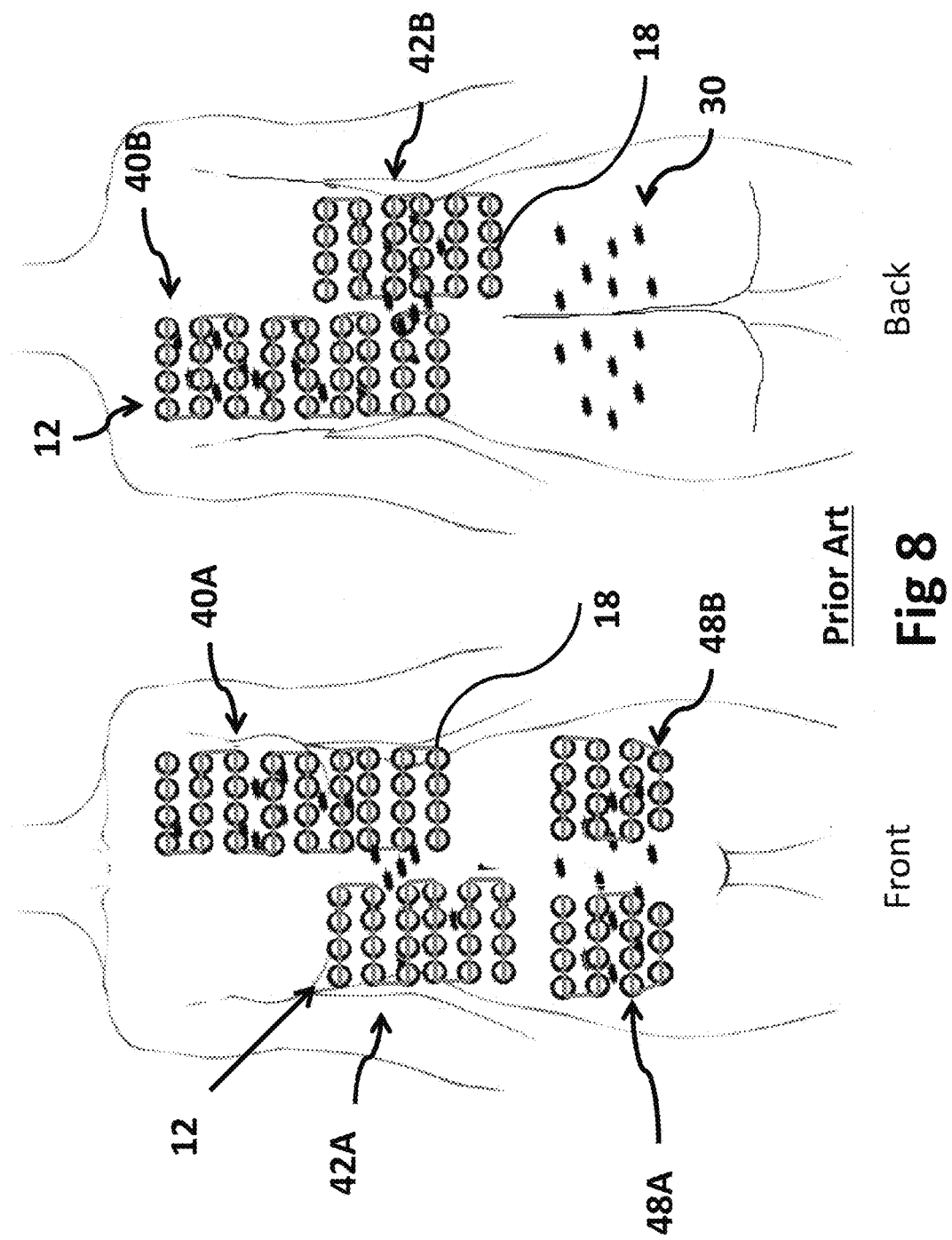
FIG. 8 illustrates an insulated electrode array that develops a co-planner field, half-Moon field, horizontally from left to right.
Figure 9:
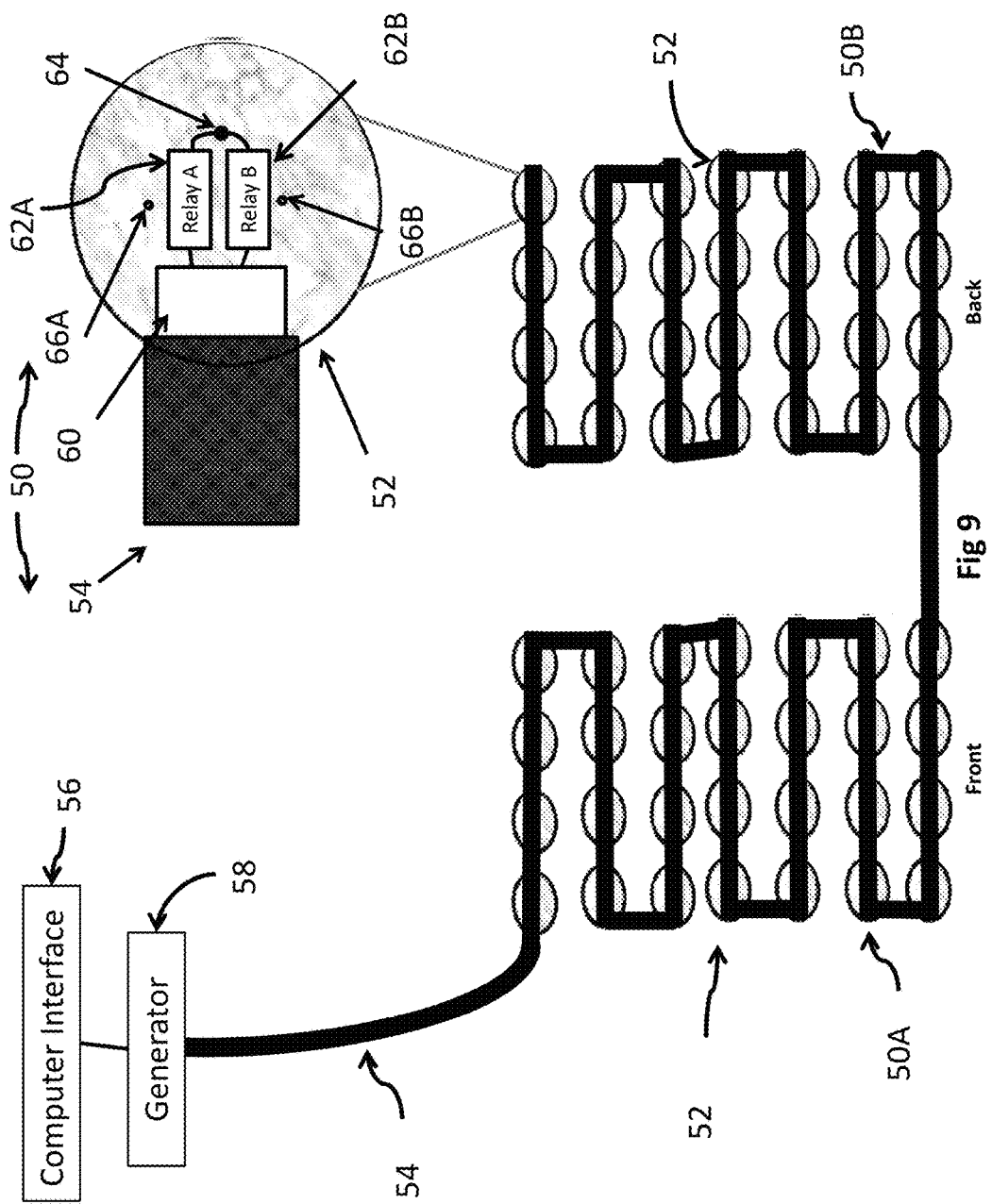
FIG. 9 is a diagram illustrating an embodiment of the present invention in the form of an insulated electrode array whereby each sub-element is programmable to energize in any array configuration and to the A sub-array or the B sub-array.

Referring now to FIG. 9, there is shown an embodiment of the present invention in the form of an insulated electrode array 50. The insulated electrode array 50, in the form of an array pair having a sub-array 50A (which for the purposes of illustration is on the front) and a sub-array 50B (illustrated on the back), includes a plurality of insulated electrode elements 52 interconnected by a multilayer flex circuit 54 to a control device 56 and a field generator 58. The multilayer flex circuit 54 in this particular embodiment contains a lead A, a lead B, a communication wire, and a ground wire (not shown for the sake of clarity). However, the multilayer flex circuit 54 is not limited to this configuration. FIG. 9 illustrates an insulated electrode array 50 where the control device 56 is programmed to send signals to the field generator 58 (including the frequency range) to be sent individually in a dynamic fashion to each of the array elements 52, as well as which of the array elements 52 are to be used in a particular configuration and sequence. One can appreciate that there are many ways to achieve dynamic reassignment of array elements when administering TTF's.

Each insulated electrode element 52 includes an integrated circuit 60 attached to two activatable switches, which may be in the form of two relays 62A (which is referred to herein as phase A) and 62B (which is referred to herein as phase B). A feed through 64 is used to interconnect the relays, 62A and 62B. Each integrated circuit 60 has a unique address. Further, each element 52 has two small low-light LED's; a first LED 66A configured to light up when phase A is being used and a second LED 66B configured to light up when phase B is being used. The desired configuration of the array elements 52 and the firing sequence are entered into the control device 56. The control device 56 may include a computer interface (not shown). The control device 56 directs each insulated electrode element 52 to turn on or off and directs it to be used for phase A or phase B of a given array. Each insulated electrode element 52 can be dynamically reassigned.

Figure 10:
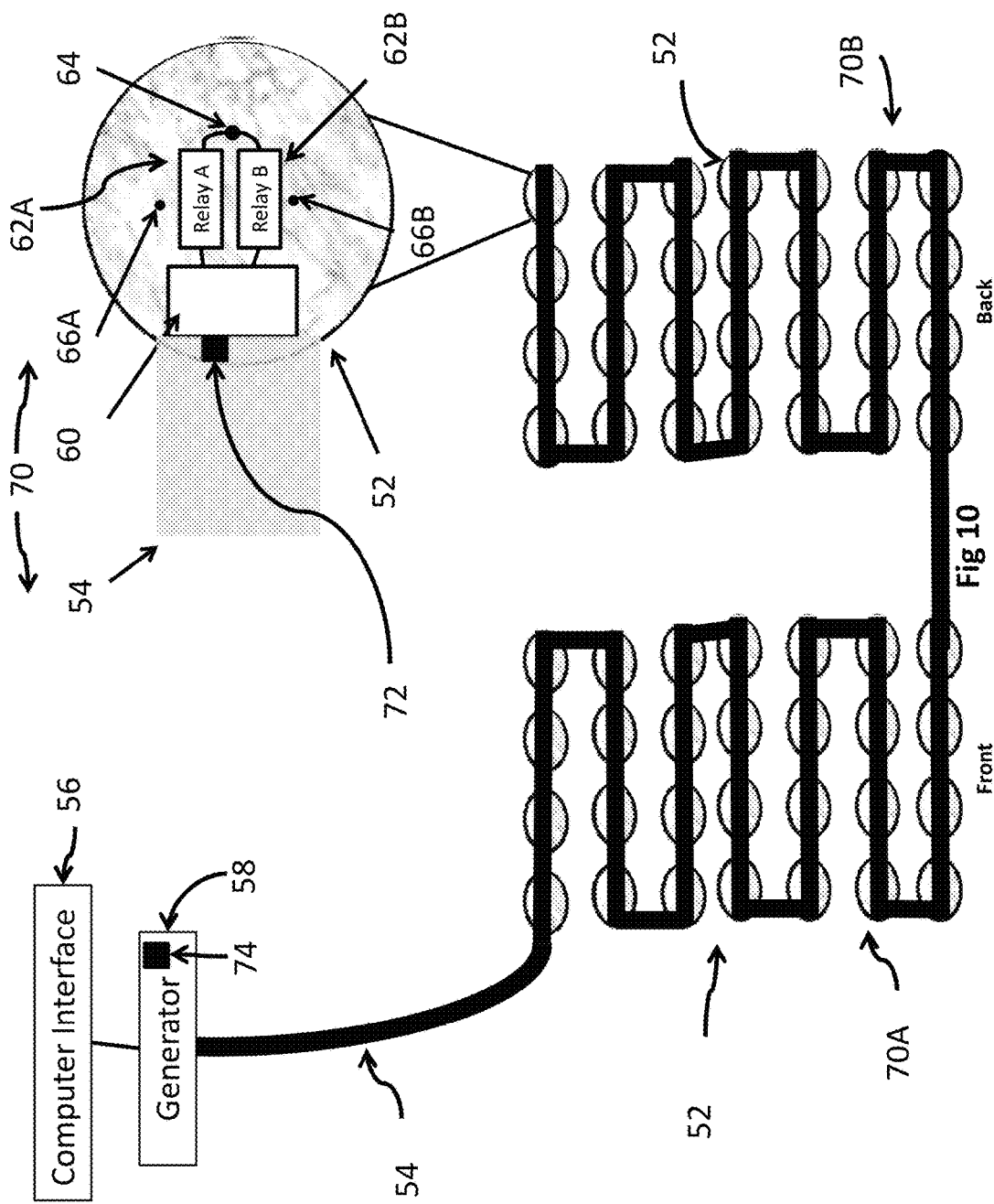
FIG. 10 is a diagram that illustrates a second embodiment of the present invention wherein the electrode elements further include a communication interface.

Now, additionally referring to FIG. 10, there is shown a second embodiment of the present invention, an insulated electrode array 70 formed by sub-arrays 70A (front) and 70B (back). In this embodiment the communication wire is not used or is removed from the multilayer flex circuit 54 and each element 52 now includes a communication interface 72 with the integrated circuit 60. A signal is sent down the A and B lead wires of the multilayer flex circuit 54 at a different frequency than the TTF to direct the desired commands to each element 52. Also, the field generator 58 includes a command generator 74 for signaling the integrated circuit 60.

Figure 11:
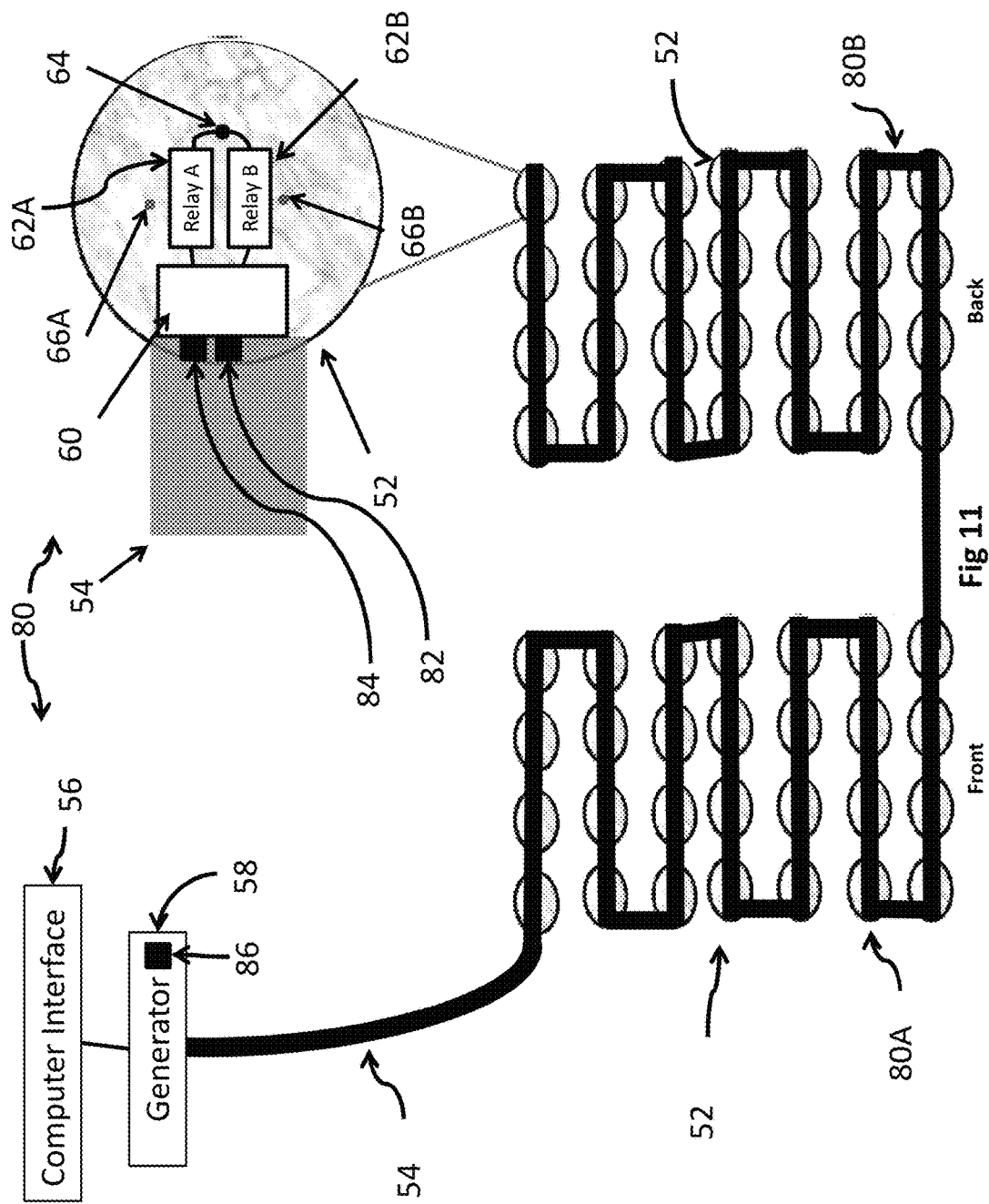
FIG. 11 illustrates a third embodiment of the present invention in which each electrode element includes a flexible wireless antenna.

Referring now to FIG. 11, there is shown a third embodiment of the present invention, an insulated electrode array 80 being formed by sub-arrays 80A (front) and 80B (back). In this embodiment, each individual element 52 includes a flexible wireless antenna 82 and a wireless communication interface 84 that enables the receiving of commands from a wireless signal generator 86 within the TTF field generator 58.

Figure 12:
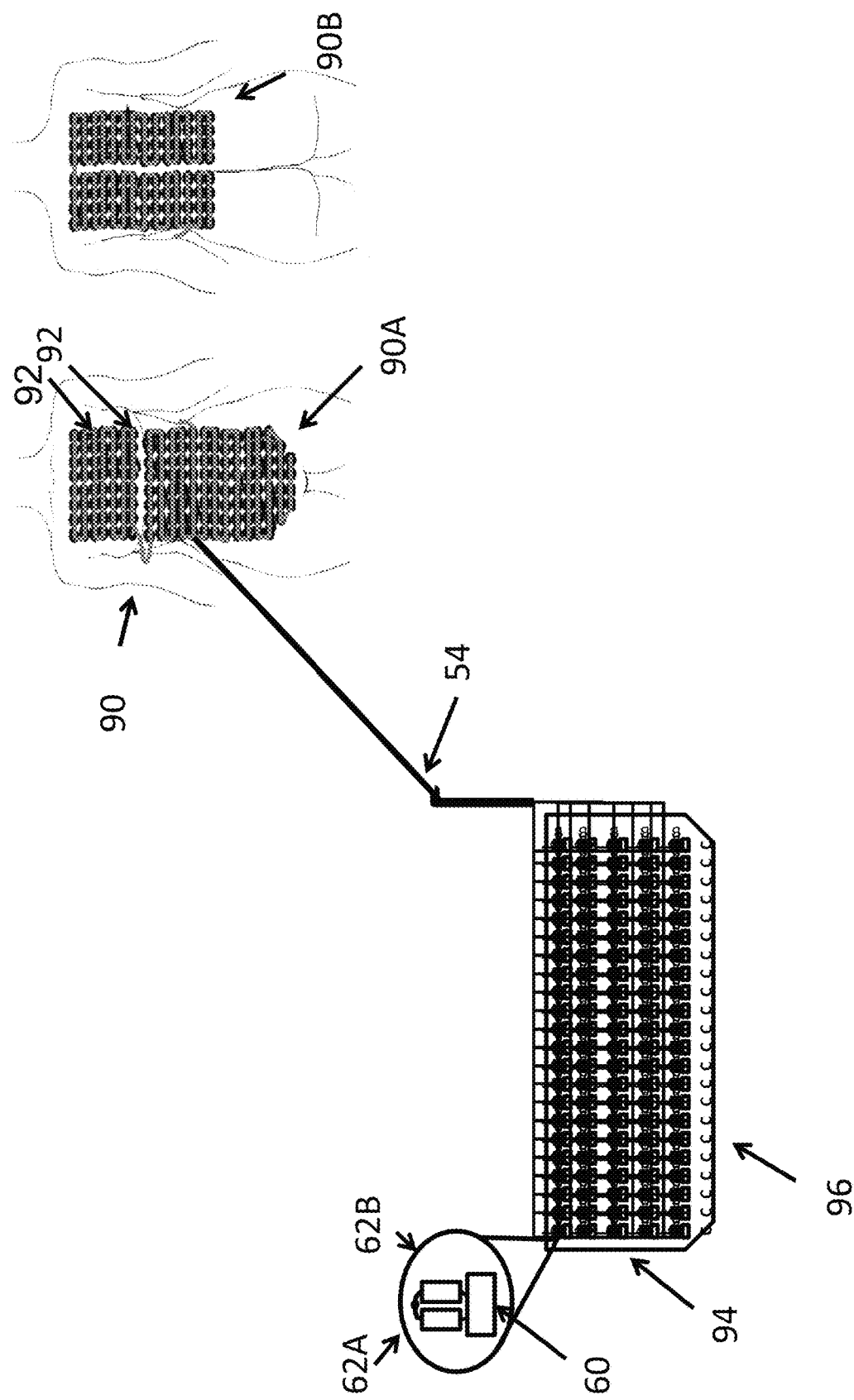
FIG. 12 is a diagram illustrating a fourth embodiment in which the integrated circuit and relays are in the same case as the field generator.

Referring now to FIG. 12, there is shown a fourth embodiment in the form of an insulated electrode array 90, a front sub-array 90A and a back sub-array 90B. In this embodiment, each integrated circuit 60 and relay pair 62A, 62B corresponding to a thin array element 92 is positioned in the same case 94 as the TTF generator 96. Thereby, the TTF generator 96 has a built-in dynamic reassignment. All the wires from the field generator 96 are run through the multilayer flex circuit 54, or any other suitable carrier, to each thin array element 92. Each thin array element 92 has its own power and communication wires (not shown). Thin array elements 92, as a result of not housing an integrated circuit 60 and relays 62A, 62B are much thinner than electrode elements 52. Thus, thin array elements 92 accommodate some patients who require less of a protrusion next to their skin. For example, thin array elements 92 cause less discomfort to obese individuals when they are sleeping.

Figure 13:
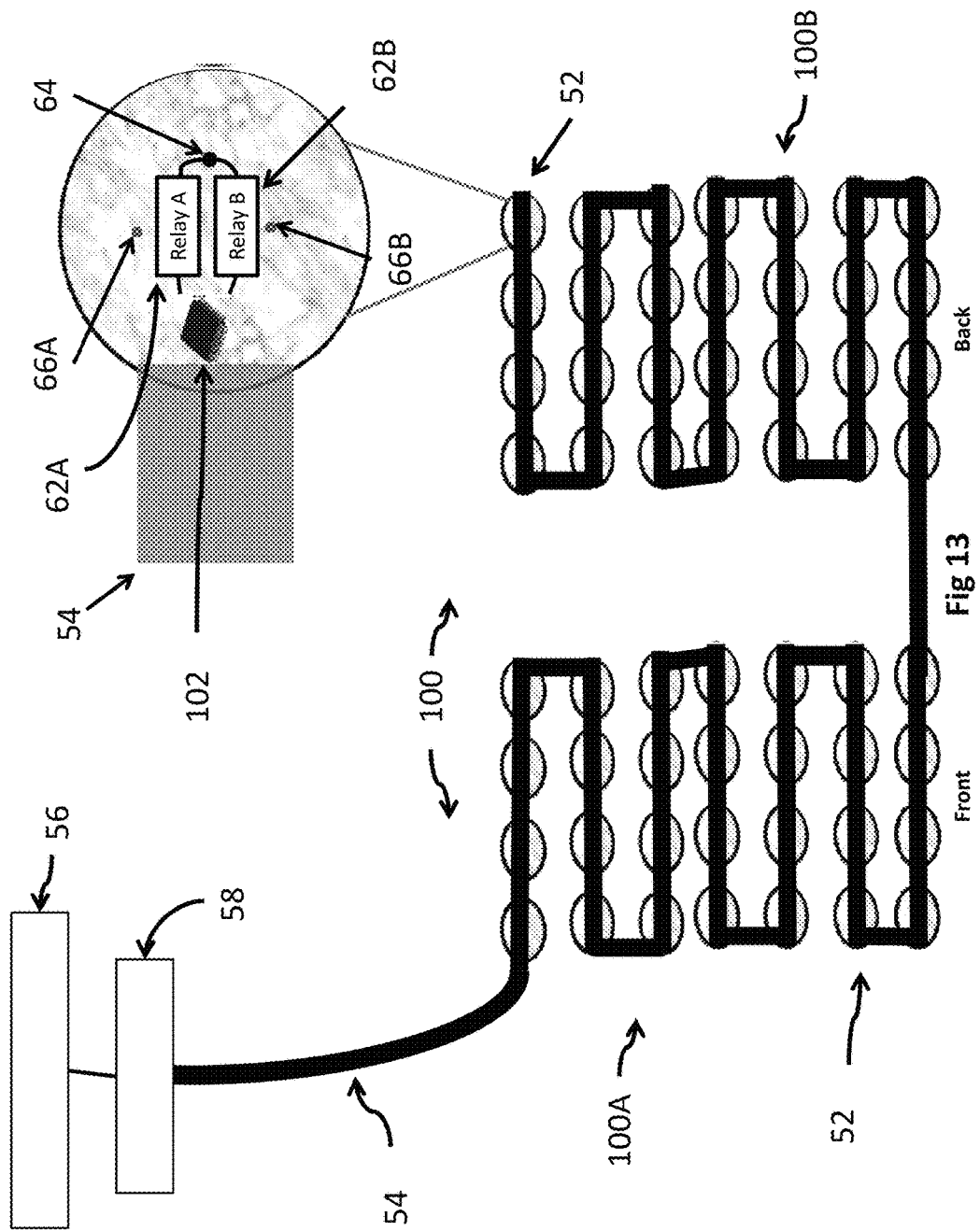
FIG. 13 illustrates a fifth embodiment according to the present invention in which each electrode element includes a microprocessor.

Referring now to FIG. 13, there is shown a fifth embodiment in the form of an insulated electrode array 100, pairing a front sub-array 100A and a back sub-array 100B. In this particular embodiment, the integrated circuit 60 is replaced by a small microprocessor 102. This embodiment allows pre-programmed firing states (array configurations and firing sequences) to be preloaded on each array element 52. This allows for broadcast communication to all array elements 52 simultaneously for faster switching. Each firing state is given a single or double digit ID. This firing ID code (or state ID) is appropriately broadcast to all array elements 52 at once. One message is sent to accomplish the firing state verses potentially hundreds using an integrated circuit alone.

Figure 14:
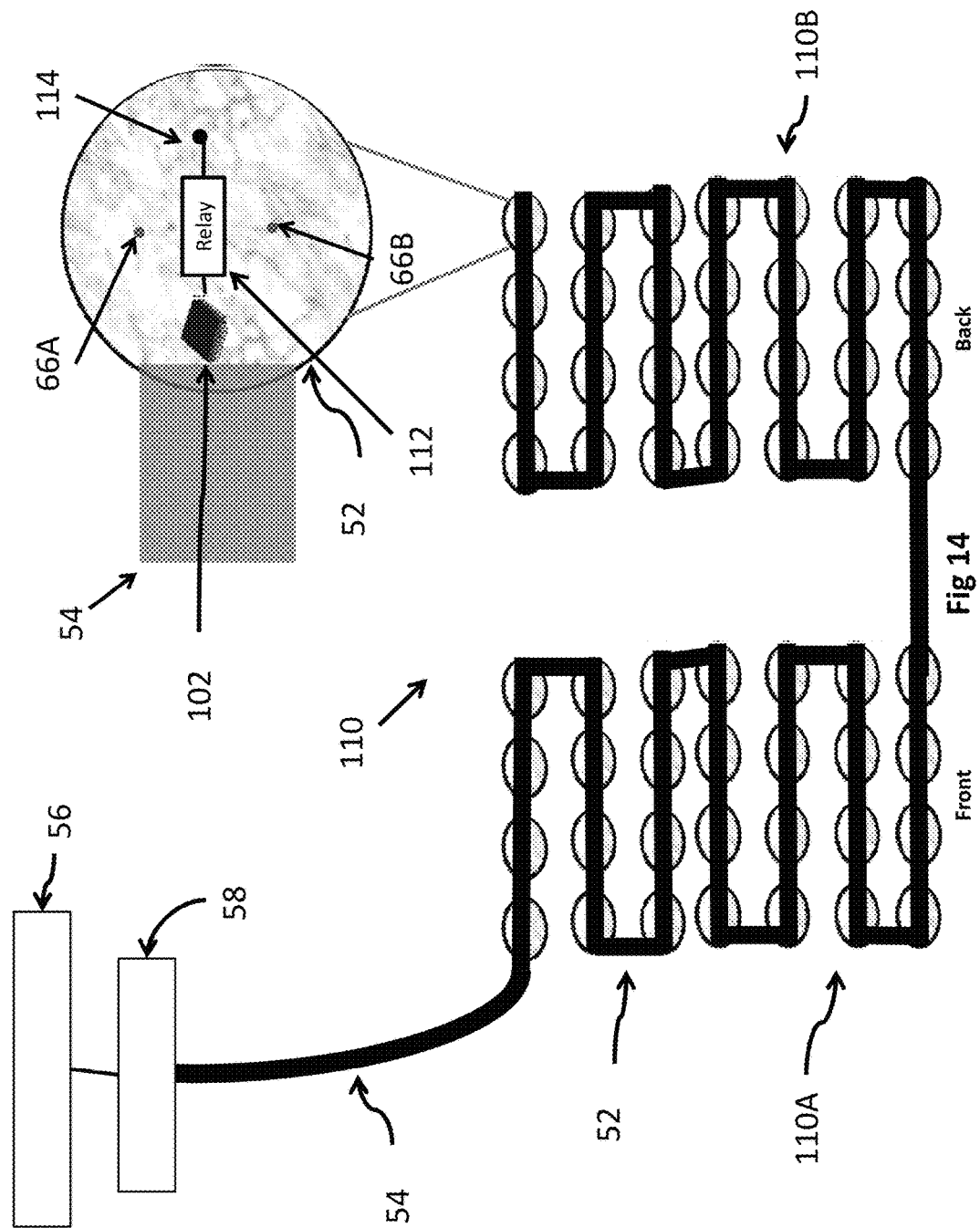
FIG. 14 is a diagram that illustrates a sixth embodiment of the present invention wherein each electrode element includes a single relay.

Referring now to FIG. 14, there is shown a sixth embodiment, an insulated electrode array 110, sub-arrays 110A (front) and 110B (back). This embodiment uses a single relay 112 per array element 52. A microprocessor 102, as shown in FIG. 14, or an integrated circuit 60 could be used to manipulate the relay 112. A feed through 114 is coupled to the relay 112 in order to supply power to each array element 52. Using relay 112 has the effect of keeping the dynamic reassignment for an array configuration, but it dedicates array elements 52 to either the A or B phase (any one of which can be on the front or back). This is useful when there is no likely need for coplanar fields.

Figure 15:
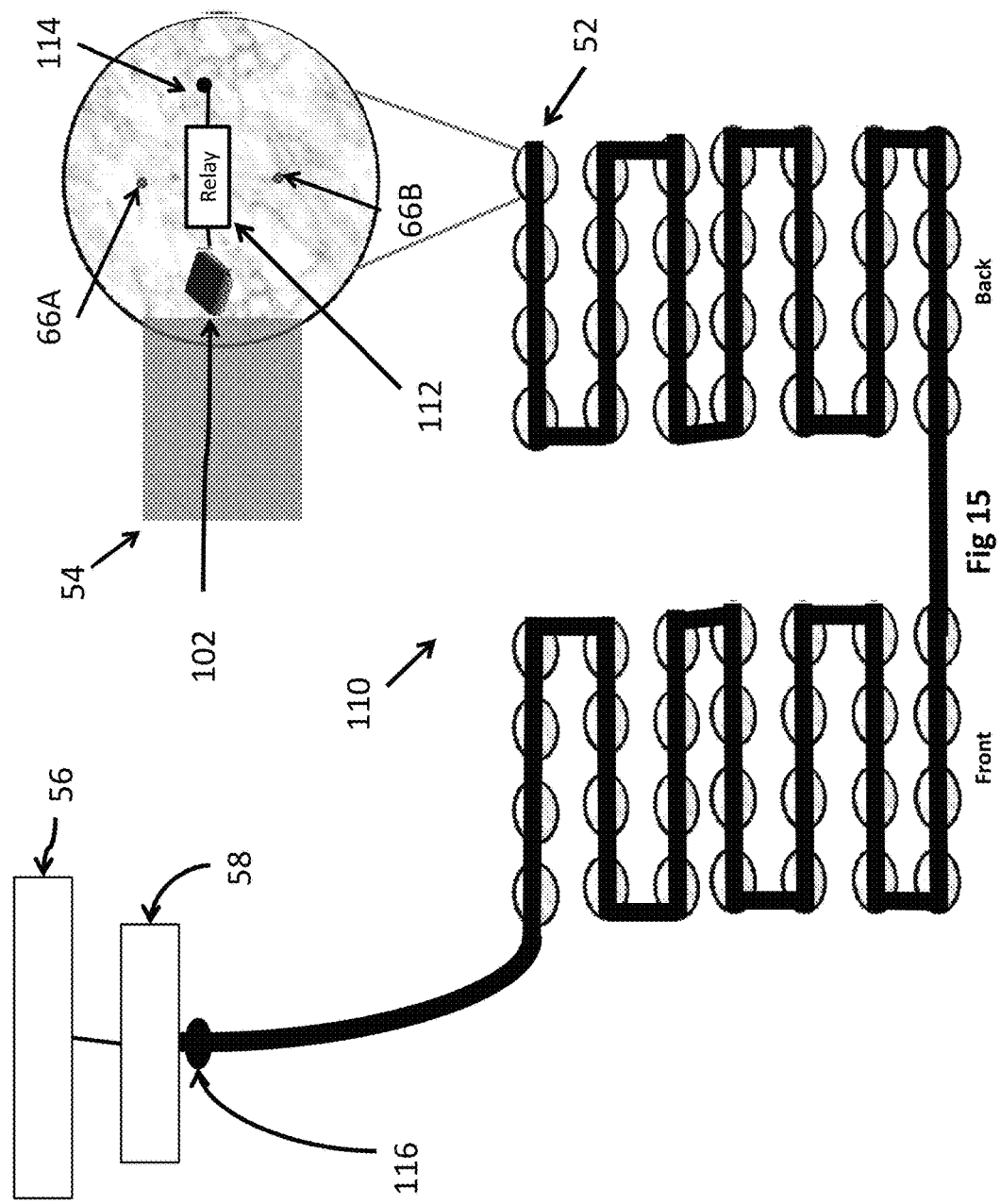
FIG. 15 is a diagram that illustrates how each embodiment may include an automatic current sensor as an extra safety precaution.

Now, additionally referring to FIG. 15, a master current sensor 116 can be used in any of the aforementioned embodiments. The master current sensor 116 is positioned at the head of a given insulated electrode array or within a given electric field generator. In other words, the master current sensor 116 is positioned upstream before the electrode array elements 52. The master current sensor 116 monitors for unusual power fluctuations that may indicate that a compromised array element 52 has allowed current to flow directly to a patients skin. In such an occurrence the master current sensor 116 would automatically shut off the entire system. Current flow directly to a body would only be at very small amperages (in most configurations a maximum of 0.13 amps). However, as this would still be undesirable it would justify an automatic shut off.

Figure 16:
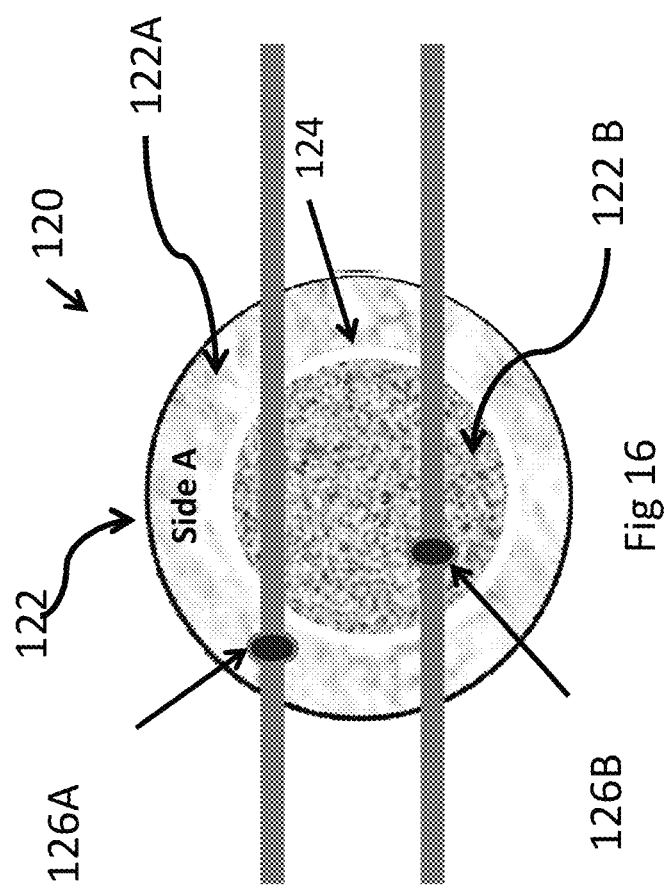
FIG. 16 is a diagram that illustrates a simplified electrode array element.

It should be appreciated that the above methods of achieving dynamic reassignment of array elements 52 when administering TTF's can be accomplished without multilayer flex circuits 54 by instead using regular wiring and small hard printed circuit boards (not shown) for each array element 52. Future embodiments may be achieved through printing switching circuitry directly into flex material. Each of the above embodiments can use intermittent messaging to avoid possible interference between the communication with array elements 52 and the actual energizing of each array element 52. All configurations can be accomplished with elements 52 of varying shapes and sizes. The number of elements 52 in a given array can be as little as 2 up to 500 or more. In addition, as shown in FIG. 16, another simplified embodiment of the present invention can utilize specially designed array elements 120 that separate the conductive area 122 that is on the insulation, which is generally a silver coating, into A and B dedicated sections, 122A and 122B respectively. The zone separator 124 helps to visualize this distinction. Also, a lead A solder point 126A and a lead B solder point 126B respectively portray the dedication to 122A, 122B sections. This embodiment yields fewer array options, but it does allow multiple uses across sides of the same elements 120.

Figure 17:
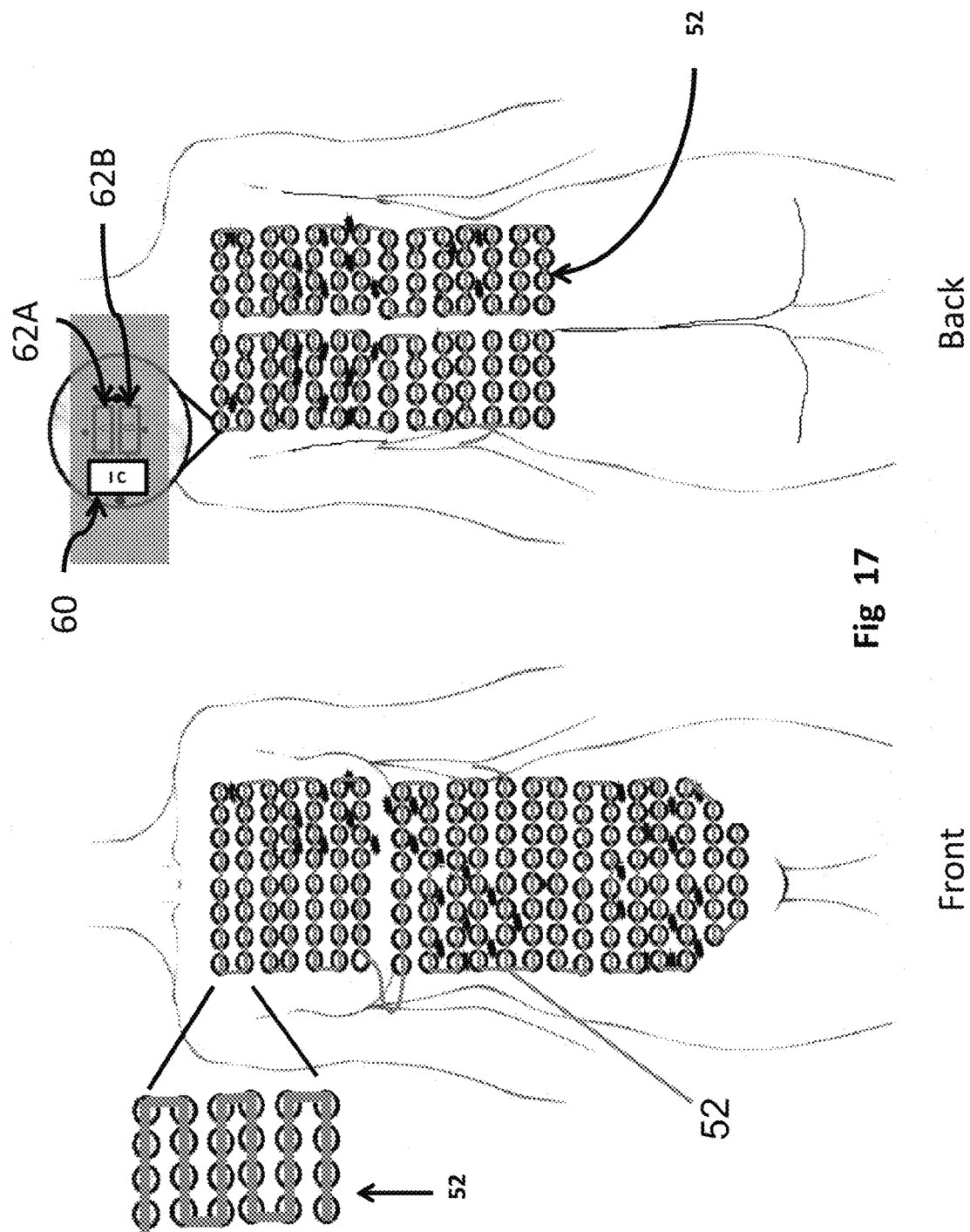
FIG. 17 is a diagram that illustrates the application of the present invention on the example patient with metastatic breast cancer that was used in FIGS. 3-8.

FIG. 17 also shows the patient with metastatic breast cancer that was used in the previous example (FIGS. 3-8). Each small insulated electrode element 52 is ready for dynamic reassignment into dynamic arrays that specifically address the cancer of this particular patient. In other words, all of the elements 52 are wired together in series with phase A and phase B, available for dynamically reassigning any array configuration to either phase A or B. The deployment of TTF's using dynamic reassignment of array elements solves many treatment issues, especially for those with metastatic disease. The dynamic assignment allows for, among other scenarios, a planar treatment regime to be used for some of the electrode elements 52, then those same elements can be reassigned to establish a field from one side of the body to the other.

Figure 18:
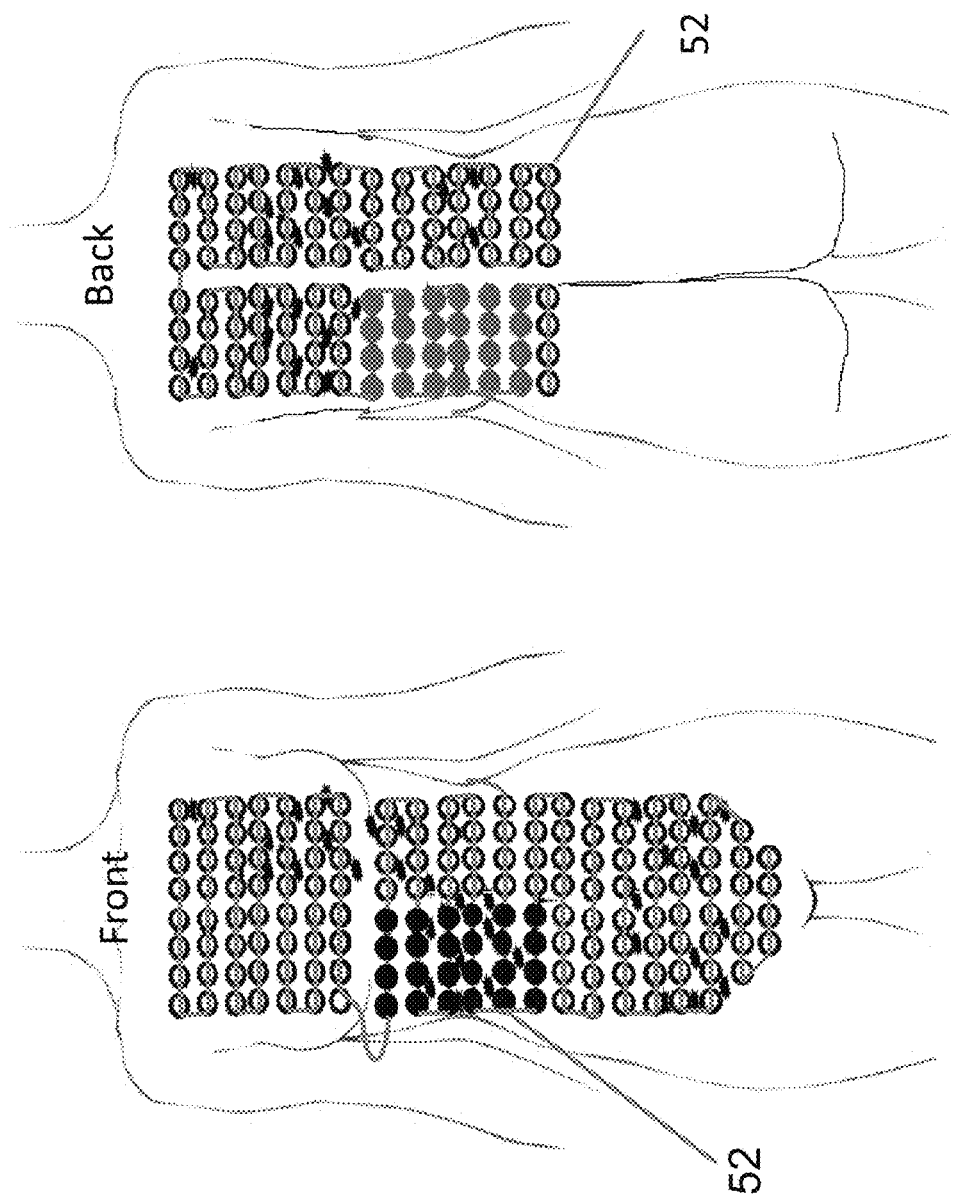
FIG. 18 illustrates the first step in a TTF 6-step treatment sequence using dynamic reassignment of array elements.
Figure 20:
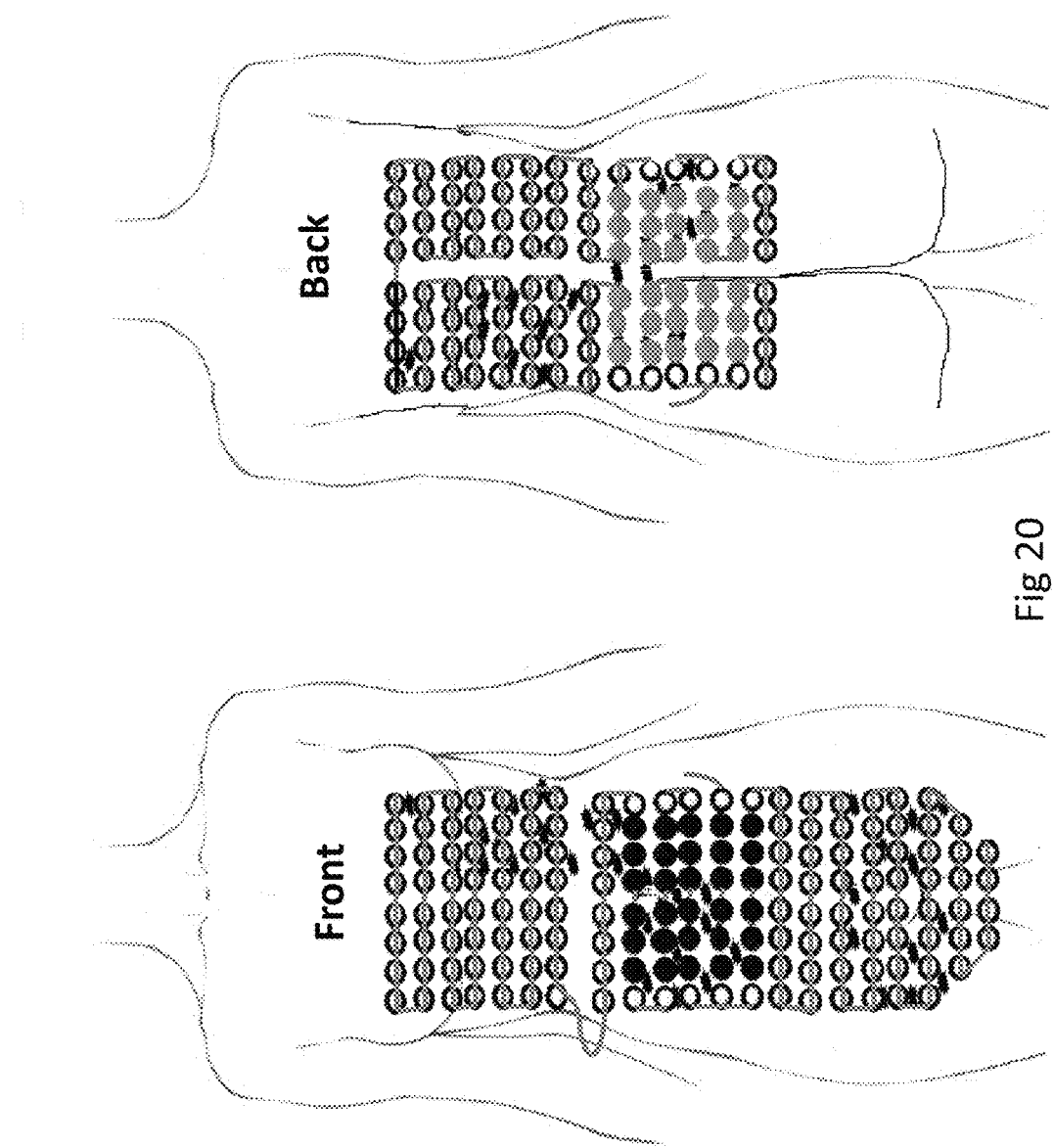
FIG. 20 illustrates the third step in the TTF 6-step treatment sequence using dynamic reassignment of array elements.
Figure 21:
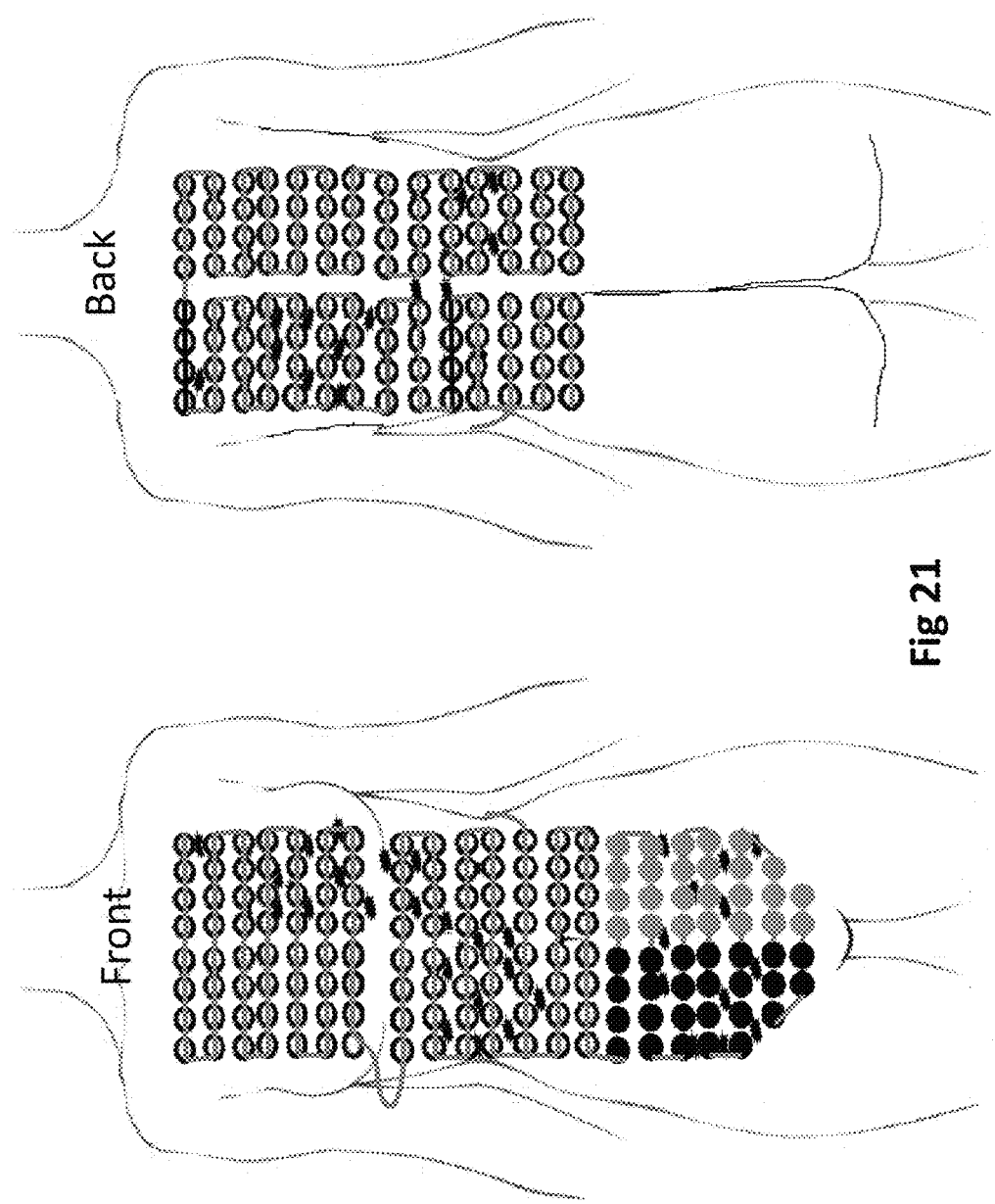
FIG. 21 illustrates the fourth step in the TTF 6-step treatment sequence using dynamic reassignment of array elements.
Figure 23:
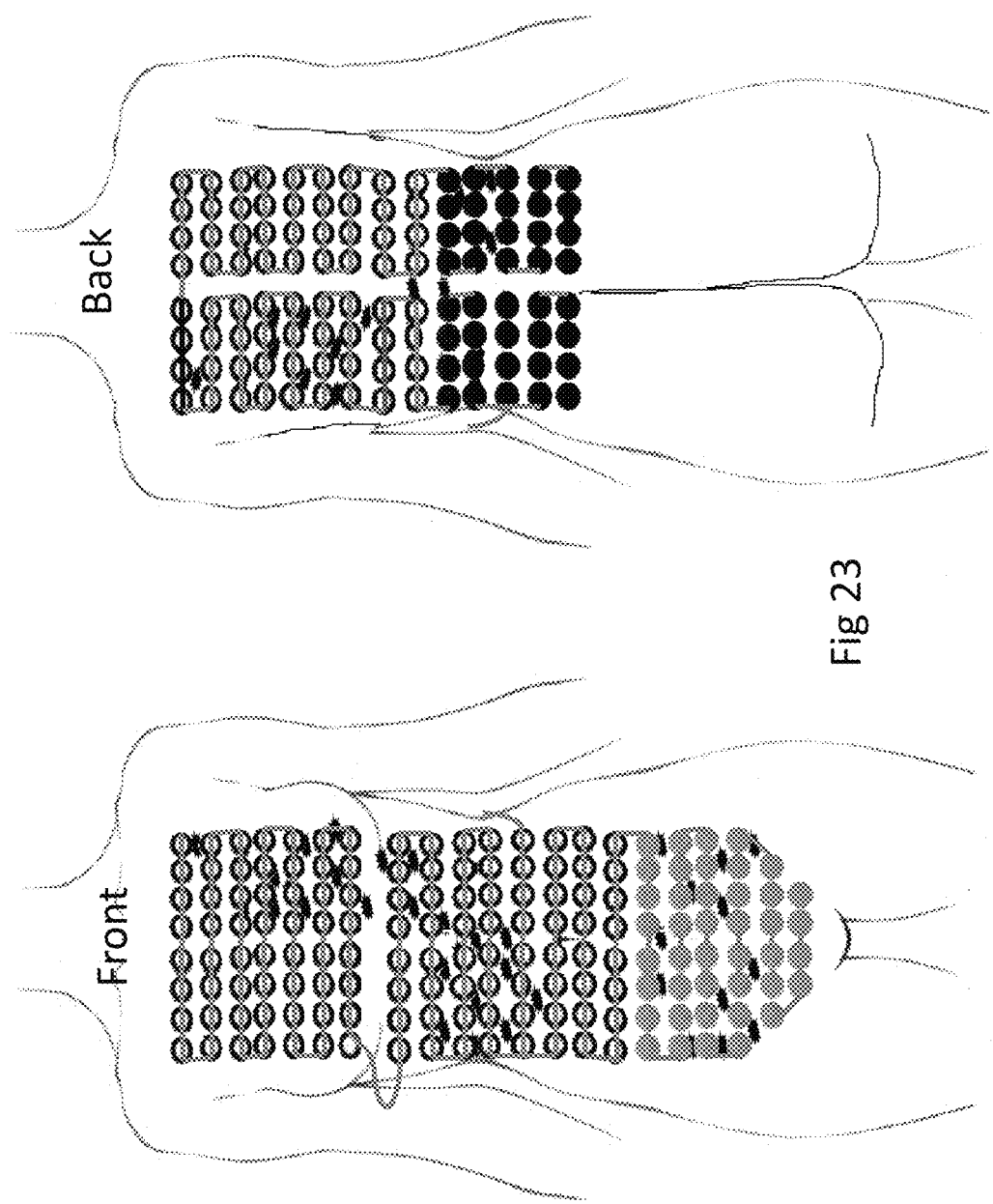
FIG. 23 illustrates the sixth step in the TTF 6-step treatment sequence using dynamic reassignment of array elements.

FIGS. 18 to 23 show a TTF treatment sequence using dynamic reassignment of array elements 52. This particular sequence uses a 6-step firing sequence taking place within a three second time span (0.5 seconds per firing). Electromagnetic arrays will be formed to treat the liver, lung and upper peritoneal cavity through the abdomen (using parallel arrays). Arrays will be formed to treat the lower peritoneal cavity with half-moon fields (coplanar arrays). Some elements will be used multiple times for different arrays and some will be used for both the A and B phases. Solid black indicates the A phase and solid gray indicates the B phase. FIG. 18 begins the treatment sequence with Step 1, treating the liver. FIG. 19 shows Step 2, treating the left lung front to back. FIG. 20 shows Step 3, treating the upper peritoneal cavity. Note, many of the same elements 52 used to form the electromagnetic array for the upper peritoneal cavity where used in the left lung and liver arrays less than 1.5 seconds ago. Dynamic reassignment allows this type of enhanced treatment for the patient. FIG. 21 shows Step 4, treating the lower peritoneal cavity with a horizontal coplanar field. FIG. 22 shows Step 5, treating the lower and upper peritoneal cavity with a vertical coplanar field. It is well known in TTF research that targeting solid tumors from different angles increases the effectiveness of treatment. As previously stated, the prior art would not allow the treatment Step 5 to be included because prior art elements have typically been dedicated to single arrays and only one power side. The above sequence incorporates elements 52 that were used in different arrays and power sides less than 1.5 seconds ago. FIG. 23 shows Step 6, treating the lower peritoneal cavity with a diagonal field through the abdomen.

The above process sequence can now be repeated or modified to target the left lung, liver and peritoneal cavity from many different angles. This is possible because of the dynamic reassignment of array elements 52 to any array configuration and either power side. The prior art does not have this kind of flexibility. The prior art runs into limitations because each element it uses is dedicated to a single array and single power side.

Figure 24:
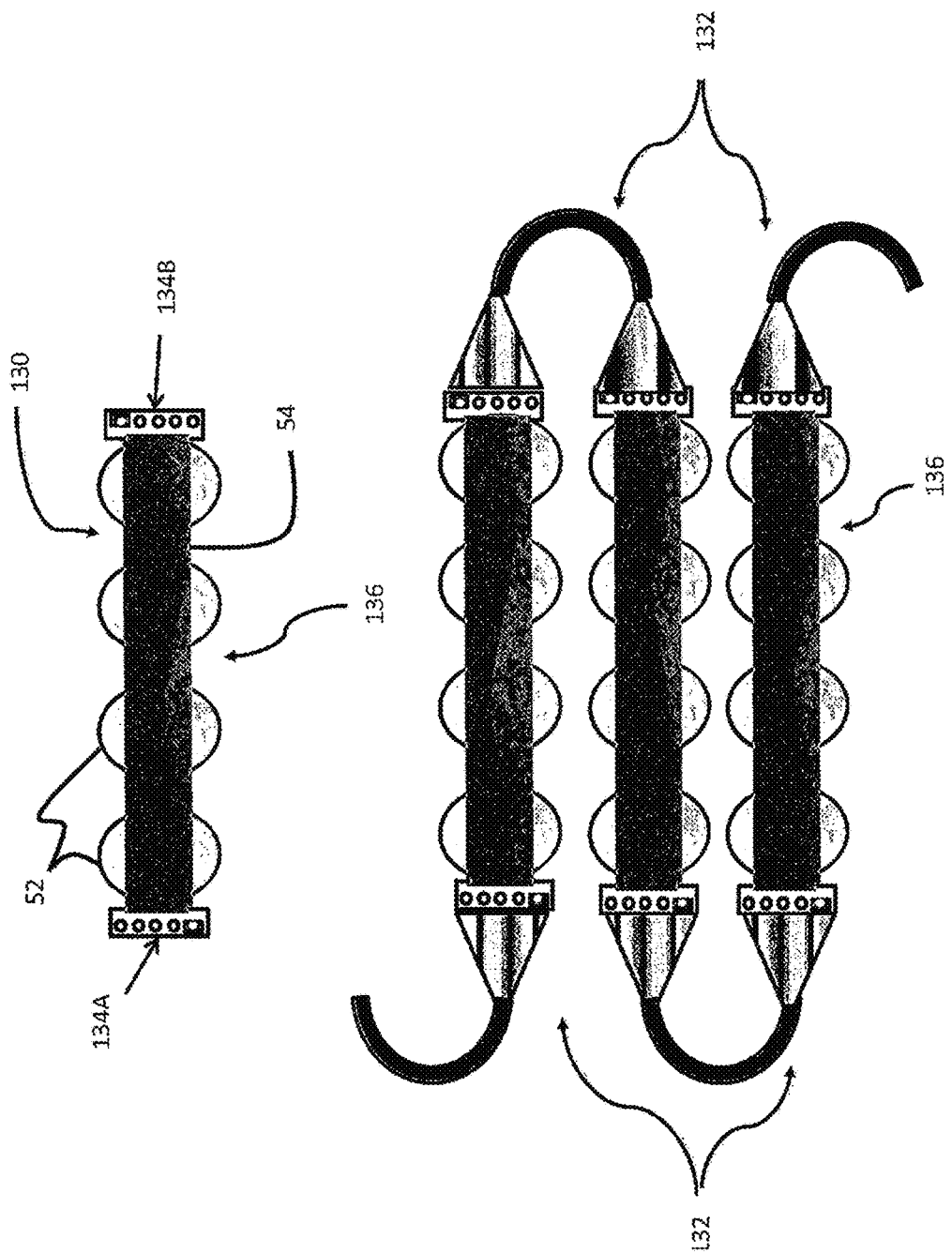
FIG. 24 is a diagram that illustrates another embodiment according to the present invention in the form of a modular system.

Referring now to FIG. 24, there is shown a custom modular system 130 using multilayer flex connectors 132. The multilayer flex connectors 132 make a modular system for adding and removing array elements 52 possible because they are able to pass heavier currents as well as low communication signals. The multilayer flex connectors 132 via respective male and female connectors 134A, 134B interconnect end-to-end element modules 136. Thus, these plugin element modules 136 can be added or subtracted at will. FIG. 24 shows a four-element module 136; however, the number of elements 52 joined end-to-end can be varied according to the present invention.

Figure 25:
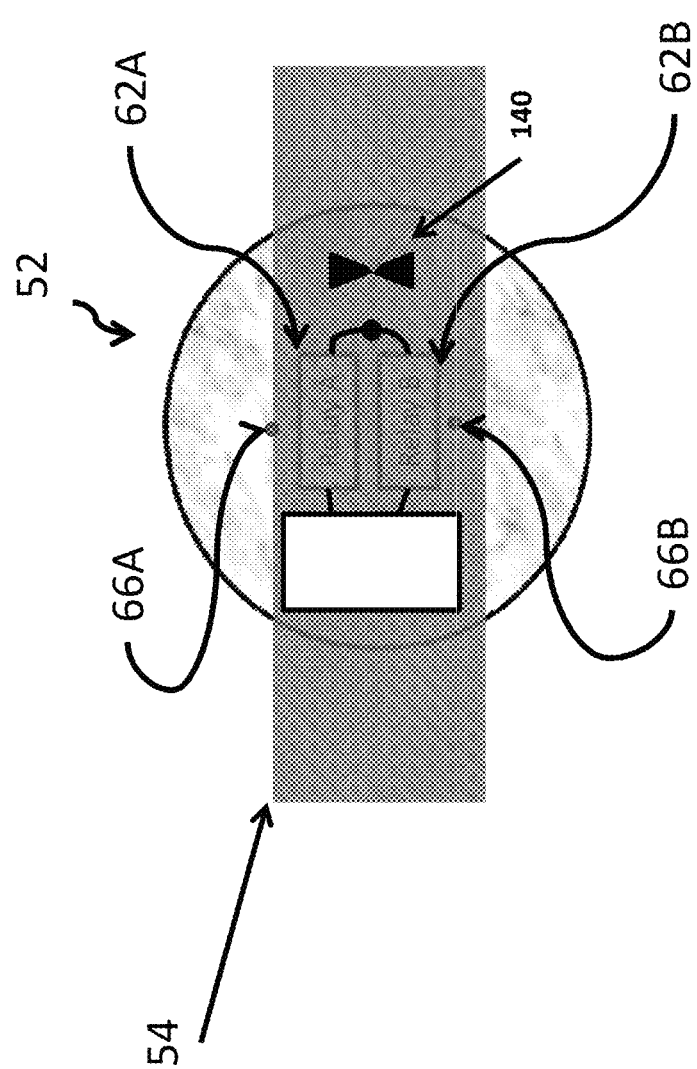
FIG. 25 is a diagram that illustrates an eighth embodiment according to the present invention in which a current monitoring sensor can be included on each electrode element.

As shown in FIG. 25, to deal with current leakage, there is included a plurality of current monitoring sensors 140 that send a shut off signal to the control device 56 if significant current fluctuation is detected. The current monitoring sensors 140 include a communication lead (not shown), and they are located on each element 52. According to the present invention, the current monitoring sensors 140 may be hardwired and/or communicate wirelessly. The current monitoring sensors 140 may also be placed at key junctures instead of on each element 52. The present invention can stop using a specific electrode element 52 if the current sensed by sensor 140 exceeds a predetermined amount. The present invention will then plan a modified regime to accomplish treatment of the patient using the remaining electrode elements 52, so that the treatments can be completed even if specific electrode elements 52 are taken off line.

Figure 26:
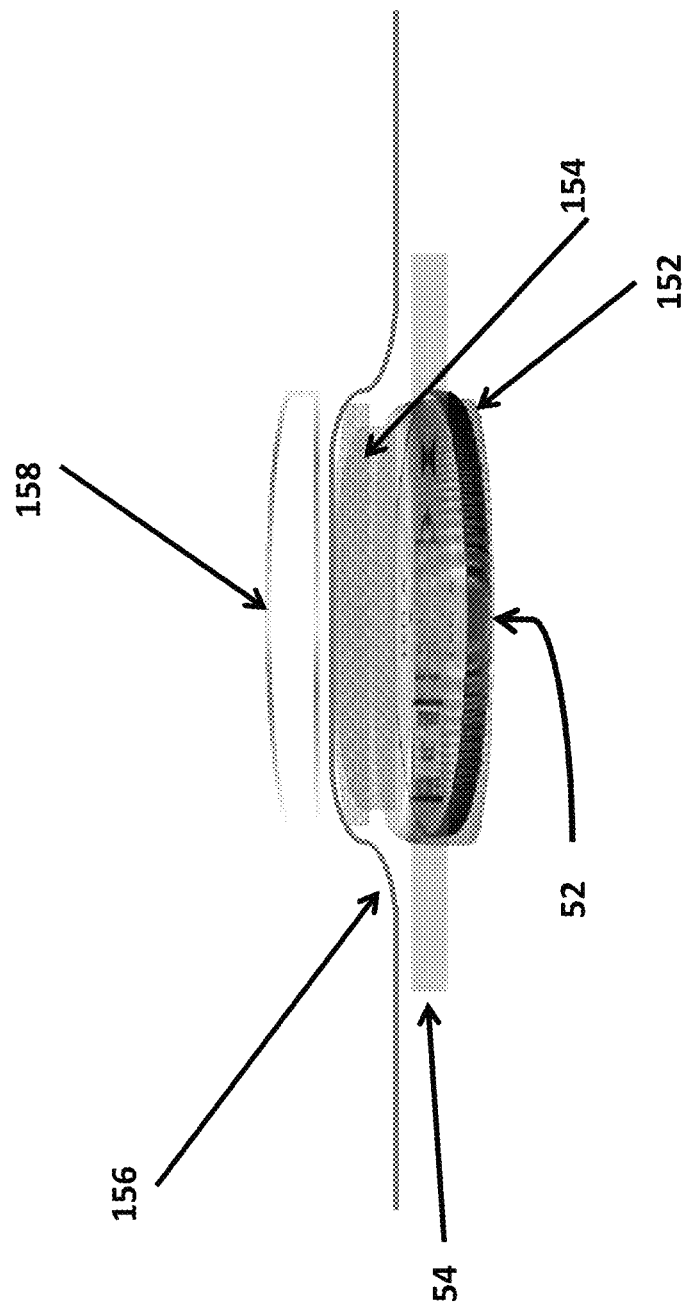
FIG. 26 is a diagram illustrating a ninth embodiment according to the present invention that prevents array migration and minimizes overall warmth.

Referring now to FIG. 26, there is shown a method and an embodiment for reducing the temperature and slipping of the array elements 52. The electronics of the insulated electrode elements 52 are encapsulated in a thermal conductive epoxy 152 with a mushroom shaped male extensions 154. The array elements 52 are attached to the patient's skin using a medical adhesive (not shown). Then a light, but tight elastic apparel article, in the form of a shirt 156, is pulled over the entire insulated electrode array. The plurality of mushroom shaped extensions 154 protrude outward from the elements 52 with the elastic shirt 156 tightly wrapped around. A conductive cap 158 is then snapped over the shirt 156 and the mushroom male extensions 154 for each element 52. The thermal conductive caps 158 conduct heat and help hold the electrode elements 52 in a more stationary position.

Figure 27:
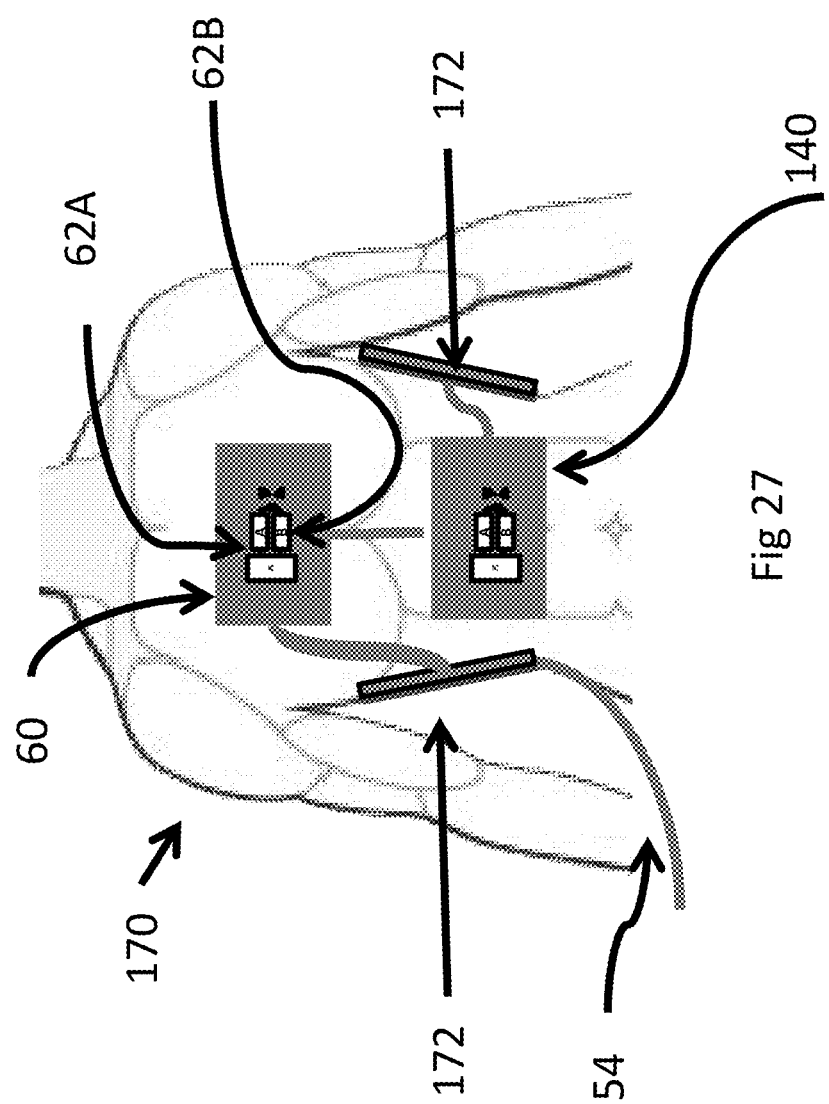
FIG. 27 is a diagram that illustrates a tenth embodiment according to the present invention incorporating large single electrode elements.

Referring now to FIG. 27, there is shown an insulated electrode array 170 having large single elements 172 that are also made to be dynamically re-assignable. The insulated electrode array 170 further includes the multilayer flex circuit 54, integrated circuits 60, relays 62A and 62B, feedthrough wires, and additionally the current monitoring sensor 140 may be included. In this embodiment there are two large electrode elements 172; however, additional large elements 172 and/or small elements 52 can also be incorporated. While arrays made up of smaller insulated electrodes, elements 52, are generally preferred in delivering TTF treatment, for reasons discussed above, large solid insulated electrodes with dynamic reassignment may also be useful in a particular treatment method.

The process for determining a firing configuration and sequence for administering TTFs when using dynamic reassignment centers upon array optimization in both body composition and treatment area. Placing an insulated electrode array on a patient's body is a unique process for each individual patient. Given an individual's body composition, a uniform application of the array elements 52 is rarely possible.

The present TTF treatment invention of dynamic reassignment of array elements 52 opens the door for full-body treatment with canvassing waves or other custom configurations. This is most beneficial and lifesaving to patients with metastatic disease, such as breast cancer that has spread to a patient's lung, pleura, liver, and pancreas at the same time. However, full-body arrays needed to deliver such treatment seldom fit on a person's body in a uniform way. The irregular nature of each person's body due to body shape, bone structure or adiposity requires placing array elements 52 at compensating angles. These angles must be compensated for with special field designs (e.g., coplanar fields). Administering TTF using the present invention's dynamic reassignment not only can accommodate irregular body shapes more affectively, but it can also do full-body sweeps throughout a patient to minimize the likelihood of reoccurring cancer.

Figure 28:
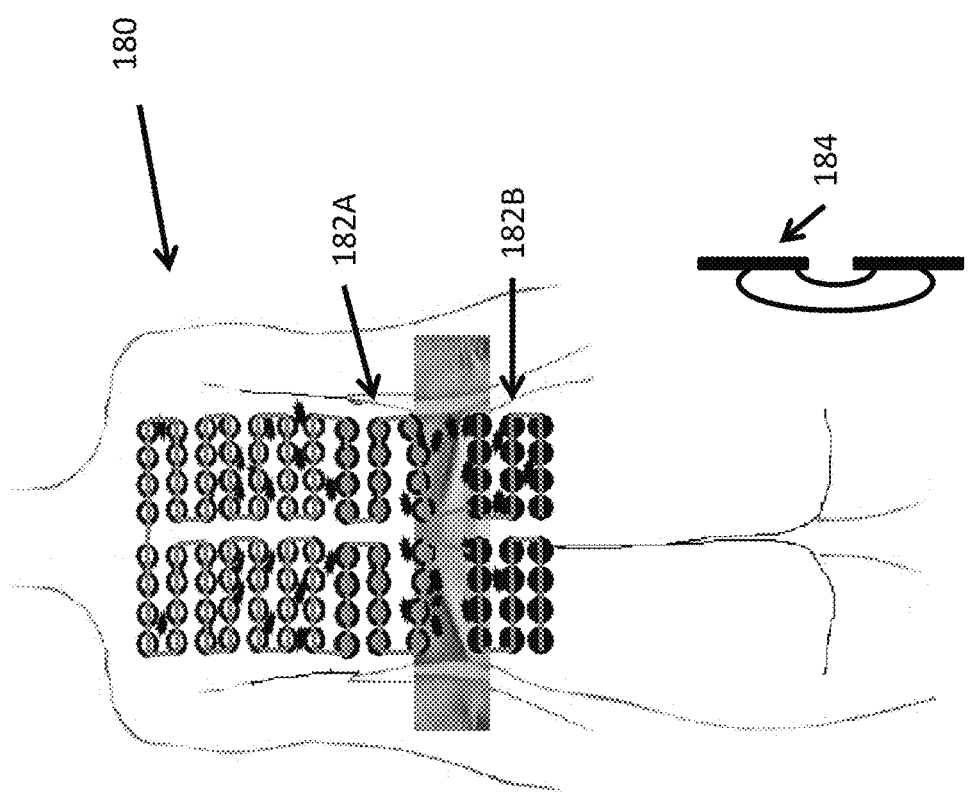
FIG. 28 is a diagram that illustrates an insulated electrode array according to the present invention used to accommodate an irregular body shape of a patient.

Referring now to FIG. 28, there is shown an example of an uneven application of a TTF insulated electrode array 180 to accommodate a person's irregular body shape. The insulated electrode array 180 uses a coplanar Phase A and Phase B, respectively 182A and 182B, to create a special coplanar field firing sequence through a patient's fat rolls. Also, there is shown the general shape of a vertical coplanar field 184 that would be created by the insulated electrode array 180.

In understanding of the embodiments of the present invention it should be appreciated that dynamic reassignments of array elements can be accomplished by assigning rows or columns of array elements 52. This can be carried out by strategically placing microprocessors and relay pairs so that they are associated with rows and/or columns instead of being associated with every disc element 52. In some configurations this approach may reduce cost of the array.

It is also contemplated that a programmable attenuator can be placed in series with the relay pairs on each array element 52 to thereby allow the power level of each array element 52 to be adjusted as needed. This is a useful feature when sharing array elements across different body widths. For example, a programmed side array meant to create a field from one side of the body to the other (the widest part of the torso in most patients) may share an array element on its edge with a programmed array to create a field over the liver from front to back. The power requirement to create a field with enough volts per centimeter to be effective may be more in the side-to-side field than in the front-to-back field. The adjustable power feature allows an adjustment of the power in a dynamic fashion to better treat tumors needing these types of custom TTF requirements.

Figure 29:
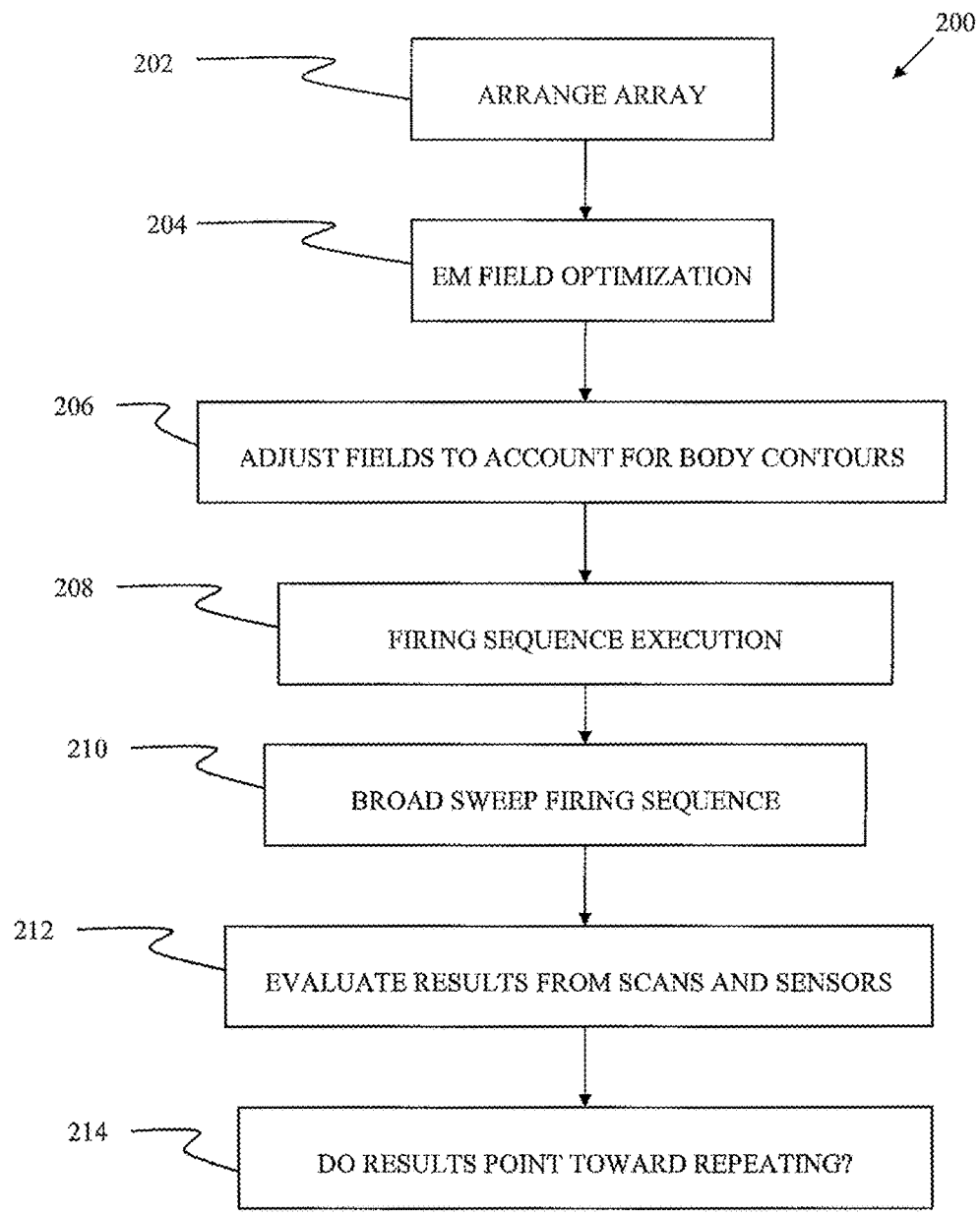
FIG. 29 is a flow chart that illustrates the unique and enhanced capabilities of TTF treatment using dynamic reassignment according to the present invention.

The phenomenon of creating special field designs to compensate body shape angles calls for a unique process of fitting a person for TTF treatment using dynamic reassignment. The flow chart in FIG. 29 outlines the unique and extra capabilities of TTF treatment using the present invention's method 200 of dynamic reassignment of array elements to any array phase A or B.

At step 202 the electrode array of one of the present invention is placed on the patient making adjustments for irregular body shapes. At step 204, the field firing design is optimized to areas most affected by cancer. The shape of the desired field is suggested by the shape, location, and spread of the cancer cells. The optimization leads to selected power levels, selection of electrodes to serve in a dynamic array, a duration of the assignment of the electrode, frequency of the signal, duration of the signal, and repetition of the signal among other possible variants.

At step 206, the field design is adjusted to accommodate irregular body shapes, such as fat rolls. This results in an optimized field coverage of the cancer areas. The firing sequence is undertaken in step 208 focused on the most active cancer areas and is continued for a prescribed duration so that the reproduction of cancer cells is interfered with by the presence of the effective electromagnetic fields. Then at step 210, a broader firing sequence focused on fringe areas is undertaken. Due to the dynamic reassignment capability of the present invention steps 208 and 210 may be interleaved, repeated multiple times per treatment, or done sequentially. After treatment the effectiveness is evaluated at step 212, to provide insight as to how to alter the characteristics of the fields for a subsequent treatment. A decision at step 214 is undertaken to conclude whether the treatment of the patient needs to continue and if so the next treatment may start at step 202 if the electrode array is removed, or at step 204 if the electrode array is left on the patient.

Use of the term "array" herein has taken different meanings, dependent upon context. In one sense when talking about the grouping of electrodes on the body it is broadly referring to the physical rows and columns of the electrodes, or at least their placement, whether in rows and columns or not. The arrays that are used in forming electromagnetic fields are dynamically selected so that the desired field can be generated and this means a subset of the electrodes that may or may not be adjacent are selected and used.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and is claimed in the claims.

What is claimed is:

1. An insulated electrode system for delivering a plurality of tumor treating electromagnetic fields, comprising:
    an array of electrode elements, each electrode element having an insulation layer that separates the electrode element from the body of a patient, each said electrode element being independently electrically accessible and configured to be dynamically assigned to emanate an electromagnetic field relative to at least one other of said electrode elements, at least one electrode element being configured to be assigned as a source electrode or as a return electrode of the electromagnetic field independent of any adjacent electrode and at least one other electrode in the array of electrode elements being configured to be assigned as a source electrode or as a return electrode of the electromagnetic field;
    wherein the system is configured to assign a first quantity of the electrodes of the array as source electrodes, and to assign a second quantity of the electrodes as return electrodes, with the first quantity being different than the second quantity; and
    wherein the electromagnetic fields are configured to treat tumors.

2. The insulated electrode system of claim 1, wherein each of said plurality of electrode elements include:
    a first LED light; and
    a second LED light, said first LED light being configured to illuminate when the electrode element is assigned to a first sub-array, said second LED light being configured to illuminate when the electrode element is assigned to a second sub-array.

3. The insulated electrode system of claim 2, wherein each of said plurality of electrode elements include:
    an activatable switch coupled to the electrode element;
    a microprocessor in communication with said activatable switch, wherein said activatable switch is dedicated to one of said first sub-array and said second sub-array.

4. The insulated electrode system of claim 1, wherein said electrode elements each include:
    a first activatable switch coupled to an electromagnetic source conductor;
    a second activatable switch coupled to an electromagnetic return conductor; and
    an integrated circuit, having a unique address, in communication with said first activatable switch and said second activatable switch for carrying out the dynamically assignment of each of said electrode elements to either the source conductor or the return conductor for delivering the tumor treating electromagnetic fields.

5. The insulated electrode system of claim 4, wherein said first activatable switch and said second activatable switch are in communication with each other by way of a feedthrough wire.

6. The insulated electrode system of claim 4, wherein each of said electrode elements additionally include a communication interface to communicate with said integrated circuit.

7. The insulated electrode system of claim 6, further comprising:
    a field generator for generating the electromagnetic field that is directed to the selected set of said electrode elements; and
    a wireless signal generator configured to send a signal to select a set of said electrode elements.

8. The insulated electrode system of claim 7, wherein each said electrode element further includes an antenna and a wireless communication interface coupled with said integrated circuit for receiving a command signal from said wireless signal generator.

9. The insulated electrode system of claim 7, further comprising a set of activatable switches with at least one of said activatable switches being correspondingly assigned to each of said electrode elements, with said set of activatable switches being proximate to and electrically coupled to said field generator.

10. The insulated electrode system of claim 1, wherein said plurality of electrode elements each include a microprocessor in communication with a first activatable switch and a second activatable switch for dynamic assignment of each of said plurality of electrode elements when administering tumor treating electric fields, wherein said microprocessor are programmed for stipulating a firing configuration and sequence that is preloaded in each said microprocessor.

11. The insulated electrode system of claim 1, further comprising a master current sensor electrically positioned upstream of said plurality of electrode elements, said master current sensor being configured to monitor the system for a power fluctuation and to trigger a shutting off of said array.

12. The insulated electrode system of claim 1, further comprising:
    a control device for dynamically programming a frequency range, a firing configuration and a firing sequence for each of said plurality of electrode elements; and
    a field generator under the control of said control device, said field generator generating an electromagnetic signal for use in said electrode elements to create the electromagnetic fields in a body of a patient.

13. The insulated electrode system of claim 12, wherein said array includes a plurality of current monitoring sensors, each said current monitoring sensor being configured to sending a shut off signal to said control device if a predetermined current fluctuation is detected in at least one electrode element, wherein each of said current monitoring sensors is positioned on a corresponding one of said plurality of electrode elements.

14. The insulated electrode system of claim 13, wherein said control device is configured to stop using said at least one electrode element for which said shut off signal has been received.

15. The insulated electrode system of claim 1, wherein said plurality of electrode elements each include a separating area or insulation between two electrically conductive sections each being assigned to one of a first sub-array and a second sub-array.

16. The insulated electrode system of claim 1, wherein said array of electrodes includes at least one of a large electrode element and a small electrode element.

17. An insulated electrode system for delivering a plurality of tumor treating electromagnetic fields, comprising:
an array of electrode elements for proximate location on a body of a patient, each electrode element having an insulation layer, each said electrode element being independently electrically accessible and configured to be dynamically assigned to emanate an electromagnetic field relative to at least one other of said electrode elements, wherein each said electrode element further includes:
a thermal conductive epoxy layer;
a mushroom shaped male extensions coupled thereto; and
a thermal conductive cap, said thermal conductive epoxy encapsulates said electrode element, said mushroom shaped male extension protrudes outwardly from said electrode element for receiving a portion of an apparel article covering said mushroom shaped male extension, said thermal conductive cap snapping over the apparel article and being retained by said mushroom male extension.

18. An insulated electrode system for delivering a plurality of tumor treating electromagnetic fields, comprising:
an array of electrode elements, each electrode element having an insulation layer that separates the electrode element from a body of a patient, each said electrode element being independently electrically accessible and configured to be dynamically assigned to emanate an electromagnetic field relative to at least one other of said electrode elements, at least one electrode element being configured to be assigned as a source electrode or as a return electrode of the electromagnetic field independent of any adjacent electrode in the array and at least one other electrode element being configured to be assigned as a source electrode or as a return electrode of the electromagnetic field; and
a field generator generating an electromagnetic field that is directed to each of the electrode elements, the field being between a source conductor and a return conductor directed to each electrode element, each of the electrode elements having:
at least one activatable switch electrically coupled to the source conductor and the return conductor; and
a circuit, having a unique address, in communication with the activatable switch for carrying out the dynamically assignment of the electrode element for delivering the tumor treating electromagnetic fields, the circuit controlling the activatable switch to electrically connect the source conductor, the return conductor or neither of the conductors to the electrode element dependent upon a command directed to the circuit having the unique address;
wherein the electromagnetic fields are configured to treat tumors.

19. The insulated electrode system of claim 18, further comprising an elastic garment arranged between the electrode elements and the conductors, the conductors being coupled to the electrode with a portion of the elastic garment therebetween.

* * * * *